US012453822B2

(12) United States Patent
Besson

(10) Patent No.: US 12,453,822 B2
(45) Date of Patent: Oct. 28, 2025

(54) AUTO-INJECTOR WITH AUDIO INDICATOR

(71) Applicant: Becton Dickinson France, Le Pont-de-Claix (FR)

(72) Inventor: Nicolas Besson, Treffort (FR)

(73) Assignee: Becton Dickinson France, Le Pont de Claix (FR)

(*) Notice: Subject to any disclaimer, the term of this patent is extended or adjusted under 35 U.S.C. 154(b) by 1057 days.

(21) Appl. No.: 17/425,982

(22) PCT Filed: Feb. 26, 2020

(86) PCT No.: PCT/EP2020/055006
§ 371 (c)(1),
(2) Date: Jul. 27, 2021

(87) PCT Pub. No.: WO2020/173993
PCT Pub. Date: Sep. 3, 2020

(65) Prior Publication Data

US 2022/0152309 A1 May 19, 2022

(30) Foreign Application Priority Data

Feb. 26, 2019 (EP) .................................... 19305224

(51) Int. Cl.
*A61M 5/315* (2006.01)

(52) U.S. Cl.
CPC ...... *A61M 5/3157* (2013.01); *A61M 5/31505* (2013.01); *A61M 2205/581* (2013.01); *A61M 2205/583* (2013.01)

(58) Field of Classification Search
CPC ............ A61M 5/3157; A61M 5/31505; A61M 2205/581; A61M 2205/583; A61M 5/326;
(Continued)

(56) References Cited

U.S. PATENT DOCUMENTS 3,562,564 A 2/1971 Potter
6,056,728 A 5/2000 Von Schuckmann
(Continued)

FOREIGN PATENT DOCUMENTS

DE 102004060146 C5 12/2015
EP 2083887 B1 2/2011
(Continued)

*Primary Examiner* — Dung T Ulsh
*Assistant Examiner* — Nelson Louis Alvarado, Jr.
(74) *Attorney, Agent, or Firm* — The Webb Law Firm

(57) ABSTRACT

A drug delivery device includes a housing, a syringe assembly including a barrel, a stopper, and a cannula, with at least a portion of the syringe assembly positioned within the housing, and a drive assembly including a plunger body configured to move the stopper within the barrel upon actuation of the drive assembly, with at least a portion of the drive assembly positioned within the housing. The plunger body has a pre-use position prior to movement of the plunger body, an injection position where the plunger body moves the stopper within the barrel, and a post use position where movement of the plunger body has stopped. The device further includes an audio indicator member configured to provide an audible indication of a transition of the plunger body from the injection position to the post-use position.

12 Claims, 26 Drawing Sheets

(58) Field of Classification Search
CPC ........ A61M 5/3202; A61M 2005/3267; A61M 5/2033; A61M 5/31578; A61M 2005/3247; A61M 5/20; A61M 5/31; A61M 5/3129; A61M 5/31501; A61M 5/31536; A61M 5/31541; A61M 5/31568; A61M 5/3213; A61M 5/3221; A61M 5/3245; A61M 2005/2006
See application file for complete search history.

(56) References Cited

U.S. PATENT DOCUMENTS 6,090,070 A 7/2000 Jager et al.
6,183,446 B1 2/2001 Jeanbourquin
6,746,429 B2 6/2004 Sadowski et al.
7,112,187 B2 9/2006 Karlsson
7,357,790 B2 4/2008 Hommann et al.
7,442,185 B2 10/2008 Amark et al.
7,563,252 B2 7/2009 Marshall et al.
7,717,877 B2 5/2010 Lavi et al.
7,879,007 B2 2/2011 Hommann
7,988,675 B2 8/2011 Gillespie, III et al.
8,021,335 B2 9/2011 Lesch, Jr.
8,038,649 B2 10/2011 Kronestedt
8,062,255 B2 11/2011 Brunnberg et al.
8,172,797 B2 5/2012 Hogdahl
8,177,745 B2 5/2012 Brechbuehler et al.
8,317,751 B2 11/2012 Habeshaw et al.
8,337,472 B2 12/2012 Edginton et al.
8,376,998 B2 2/2013 Daily et al.
8,409,149 B2 4/2013 Hommann et al.
8,496,619 B2 7/2013 Kramer et al.
8,579,866 B2 11/2013 Morgan et al.
8,679,061 B2 3/2014 Julian et al.
8,715,246 B2 5/2014 Giambattista et al.
8,747,357 B2 6/2014 Stamp et al.
8,758,301 B2 6/2014 Shang et al.
8,915,882 B2 12/2014 Cabiri
8,932,254 B2 1/2015 Eaton
8,945,049 B2 2/2015 Hommann et al.
8,956,331 B2 2/2015 Johansen et al.
8,968,236 B2 3/2015 Jennings et al.
8,992,477 B2 3/2015 Raday et al.
8,998,855 B2 4/2015 Hudson et al.
9,011,375 B2 4/2015 Holmqvist et al.
9,033,932 B2 5/2015 Holmqvist
9,072,833 B2 7/2015 Jennings et al.
9,078,978 B2 7/2015 Schraga
9,084,849 B2 7/2015 Edwards et al.
9,125,988 B2 9/2015 Karlsson
9,180,256 B2 11/2015 Eaton
9,180,259 B2 11/2015 Lesch, Jr.
9,186,462 B2 11/2015 Lanzi et al.
9,199,038 B2 12/2015 Daniel
9,199,041 B2 12/2015 Edginton
9,205,199 B2 12/2015 Kemp et al.
9,216,251 B2 12/2015 Daniel
9,233,213 B2 1/2016 Olson et al.
9,259,536 B2 2/2016 Gillespie, III et al.
9,302,047 B2 4/2016 Alexandersson
9,327,084 B2 5/2016 Evans
9,352,099 B2 5/2016 Roberts et al.
9,358,345 B2 6/2016 Brereton et al.
9,364,610 B2 6/2016 KraMer et al.
9,364,611 B2 6/2016 KraMer et al.
9,427,528 B2 8/2016 Hommann et al.
9,427,531 B2 8/2016 Hourmand et al.
9,446,195 B2 9/2016 Kramer et al.
9,486,583 B2 11/2016 Lannan et al.
9,522,233 B2 12/2016 Bicknell et al.
9,526,837 B2 12/2016 Carrel et al.
9,533,099 B2 1/2017 Maritan
9,533,102 B2 1/2017 Lesch, Jr.
9,586,011 B2 3/2017 Roberts et al.
9,604,011 B2 3/2017 Roberts et al.
9,616,181 B2 4/2017 Kemp et al.
9,629,959 B2 4/2017 Lesch
9,724,480 B2 8/2017 Harms et al.
9,744,306 B2 8/2017 Cowe
9,764,092 B2 9/2017 Cabiri
9,764,101 B2 9/2017 McLoughlin et al.
9,775,948 B2 10/2017 Bechmann et al.
9,789,257 B2 10/2017 Travanty
9,833,579 B2 12/2017 Pedersen et al.
9,855,392 B2 1/2018 Hommann et al.
9,867,942 B2 1/2018 Alexandersson
9,867,949 B2 1/2018 Sund et al.
9,872,961 B2 1/2018 Fourt et al.
9,901,674 B2 2/2018 McLoughlin et al.
9,913,943 B2 3/2018 Fourt et al.
9,925,342 B2 3/2018 Carrel et al.
RE46,789 E 4/2018 Olson
9,950,125 B2 4/2018 Wotton et al.
9,956,353 B2 5/2018 Rao et al.
9,974,904 B2 5/2018 Burk et al.
9,981,084 B2 5/2018 Kadamus et al.
9,987,436 B2 6/2018 Giambattista et al.
9,999,734 B2 6/2018 Cowe
10,004,852 B2 6/2018 Marsh et al.
10,046,115 B2 8/2018 Bokelman et al.
10,080,847 B2 9/2018 Roberts et al.
10,086,145 B2 10/2018 Cabiri et al.
10,086,152 B2 10/2018 Imai et al.
10,092,073 B2 10/2018 Wagoner
10,092,698 B2 10/2018 Park et al.
10,092,703 B2 10/2018 Mounce et al.
10,105,496 B2 10/2018 Aneas
10,118,001 B2 11/2018 Fourt et al.
10,130,774 B2 11/2018 Daniel
10,137,255 B2 11/2018 Kemp
10,137,256 B2 11/2018 Taal et al.
10,149,939 B2 12/2018 Giambattista et al.
10,159,791 B2 12/2018 Guillermo
10,159,800 B2 12/2018 Säll
10,183,121 B2 1/2019 Cowe
10,252,005 B2 4/2019 Row et al.
10,272,210 B2 4/2019 Keitel
10,300,218 B2 5/2019 Stefanov
10,307,545 B2 6/2019 Maxfield
10,322,237 B2 6/2019 Fabien
10,335,553 B2 7/2019 Bendek
10,350,356 B2 7/2019 Hirschel et al.
10,363,377 B2 7/2019 Atterbury et al.
10,363,378 B2 7/2019 Moore
10,376,641 B2 8/2019 Hirschel et al.
10,384,009 B2 8/2019 Olson et al.
10,406,294 B2 9/2019 Ward et al.
10,417,937 B2 9/2019 Gaillot et al.
10,485,934 B2 11/2019 Bostrom
10,493,212 B2 12/2019 Tschirren et al.
10,493,213 B2 12/2019 Hommann et al.
10,500,337 B2 12/2019 Fabien et al.
10,525,201 B2 1/2020 Brunnberg et al.
10,561,798 B2 2/2020 Holland et al.
10,589,027 B2 * 3/2020 Fabien ................ A61M 5/2033
10,643,744 B2 5/2020 Hopper et al.
10,646,643 B2 5/2020 Cabiri et al.
10,758,683 B2 9/2020 Gibson et al.
10,799,647 B2 10/2020 Hostettler et al.
10,821,072 B2 11/2020 Wotton et al.
10,881,799 B2 1/2021 Hirschel et al.
10,888,668 B2 1/2021 Mosebach et al.
10,894,127 B2 1/2021 Tschirren et al.
10,912,890 B2 2/2021 Gaillot et al.
10,918,798 B2 2/2021 Helmer
10,967,128 B2 4/2021 Holmqvist
10,973,984 B2 4/2021 Fournier et al.
11,040,145 B1 6/2021 Chu
11,097,065 B2 8/2021 Newton et al.
11,103,647 B2 8/2021 Bernhard et al.
11,141,542 B2 10/2021 Chu et al.
11,147,932 B2 10/2021 Alexandersson
11,246,987 B2 2/2022 Cowe et al.
2003/0105430 A1 6/2003 Lavi et al.

(56) References Cited

U.S. PATENT DOCUMENTS

| | | | | |
|---|---|---|---|---|
| 2005/0222539 | A1 | 10/2005 | Gonzales et al. | |
| 2011/0092915 | A1* | 4/2011 | Olson | A61M 5/326 604/198 |
| 2011/0196339 | A1* | 8/2011 | Hirschel | A61M 5/2033 604/506 |
| 2013/0065153 | A1 | 3/2013 | Bae et al. | |
| 2013/0331796 | A1 | 12/2013 | Wozencroft | |
| 2014/0128808 | A1 | 5/2014 | Keitel | |
| 2015/0088077 | A1 | 3/2015 | Kemp et al. | |
| 2015/0202379 | A1 | 7/2015 | Raday et al. | |
| 2015/0273162 | A1 | 10/2015 | Holmqvist | |
| 2016/0030675 | A1 | 2/2016 | Draper et al. | |
| 2016/0074584 | A1 | 3/2016 | Carmel et al. | |
| 2016/0074585 | A1 | 3/2016 | Hommann et al. | |
| 2016/0106929 | A1 | 4/2016 | Fournier et al. | |
| 2016/0129195 | A1 | 5/2016 | Jennings et al. | |
| 2016/0129200 | A1 | 5/2016 | Jennings et al. | |
| 2016/0151586 | A1 | 6/2016 | Kemp | |
| 2016/0175523 | A1 | 6/2016 | Blomberg | |
| 2016/0199588 | A1 | 7/2016 | Kemp | |
| 2016/0199589 | A1 | 7/2016 | Plumptre | |
| 2016/0220761 | A1 | 8/2016 | Shetty et al. | |
| 2016/0303323 | A1 | 10/2016 | Saussaye et al. | |
| 2016/0303327 | A1 | 10/2016 | Moren | |
| 2016/0317750 | A1 | 11/2016 | Jugl et al. | |
| 2016/0317753 | A1 | 11/2016 | Jugl et al. | |
| 2016/0325044 | A1 | 11/2016 | Tschirren et al. | |
| 2017/0007764 | A1 | 1/2017 | Saussaye | |
| 2017/0021103 | A1 | 1/2017 | Mosebach et al. | |
| 2017/0043103 | A1 | 2/2017 | Wotton et al. | |
| 2017/0072142 | A1 | 3/2017 | Perthu | |
| 2017/0080163 | A1 | 3/2017 | Bendek et al. | |
| 2017/0136192 | A1 | 5/2017 | Stefansen et al. | |
| 2017/0173270 | A1 | 6/2017 | Nakamura et al. | |
| 2017/0182242 | A1 | 6/2017 | Galitz et al. | |
| 2017/0203041 | A1 | 7/2017 | Julian et al. | |
| 2017/0224921 | A1 | 8/2017 | Takabatake et al. | |
| 2017/0252518 | A1 | 9/2017 | Holmqvist | |
| 2017/0258998 | A1 | 9/2017 | Stamp | |
| 2017/0290990 | A1 | 10/2017 | Wu | |
| 2017/0340824 | A1 | 11/2017 | Maritan | |
| 2017/0361015 | A1 | 12/2017 | McCullough | |
| 2017/0361021 | A1 | 12/2017 | Wotton et al. | |
| 2018/0015223 | A1 | 1/2018 | Aeschlimann | |
| 2018/0028753 | A1 | 2/2018 | Wilmot et al. | |
| 2018/0036491 | A1 | 2/2018 | Maxfield | |
| 2018/0036492 | A1 | 2/2018 | Schader et al. | |
| 2018/0043108 | A1 | 2/2018 | Mesa et al. | |
| 2018/0078713 | A1 | 3/2018 | Hommann et al. | |
| 2018/0079119 | A1 | 3/2018 | Morris et al. | |
| 2018/0093046 | A1 | 4/2018 | Hourmand et al. | |
| 2018/0099099 | A1 | 4/2018 | Sund et al. | |
| 2018/0110926 | A1 | 4/2018 | Schrul et al. | |
| 2018/0110936 | A1 | 4/2018 | Hatch et al. | |
| 2018/0126083 | A1 | 5/2018 | Schmid et al. | |
| 2018/0133407 | A1 | 5/2018 | Kemp et al. | |
| 2018/0140781 | A1 | 5/2018 | Kemp et al. | |
| 2018/0140782 | A1 | 5/2018 | Kemp et al. | |
| 2018/0147358 | A1 | 5/2018 | Julian et al. | |
| 2018/0154078 | A1 | 6/2018 | Mosebach et al. | |
| 2018/0154085 | A1 | 6/2018 | Mosebach et al. | |
| 2018/0154089 | A1 | 6/2018 | Mosebach et al. | |
| 2018/0161504 | A1 | 6/2018 | Kemp et al. | |
| 2018/0169342 | A1 | 6/2018 | Mosebach et al. | |
| 2018/0169349 | A1 | 6/2018 | Mosebach et al. | |
| 2018/0177952 | A1 | 6/2018 | Bengtsson et al. | |
| 2018/0200445 | A1 | 7/2018 | Brereton et al. | |
| 2018/0207363 | A1 | 7/2018 | Fabien et al. | |
| 2018/0221589 | A1 | 8/2018 | Vogt et al. | |
| 2018/0243506 | A1 | 8/2018 | Niven et al. | |
| 2018/0256826 | A1 | 9/2018 | Roberts et al. | |
| 2018/0264196 | A1 | 9/2018 | Fabien et al. | |
| 2018/0289899 | A1 | 10/2018 | Gould | |
| 2018/0296768 | A1 | 10/2018 | Gould et al. | |
| 2018/0304014 | A1 | 10/2018 | Knudsen et al. | |
| 2018/0311438 | A1 | 11/2018 | Stamp et al. | |
| 2018/0326152 | A1 | 11/2018 | Laiosa | |
| 2018/0344946 | A1 | 12/2018 | Scharf | |
| 2018/0353705 | A1 | 12/2018 | Andre et al. | |
| 2018/0369497 | A1 | 12/2018 | Schader et al. | |
| 2019/0151547 | A1 | 5/2019 | Cowe et al. | |
| 2019/0151564 | A1 | 5/2019 | Schrul et al. | |
| 2019/0151565 | A1 | 5/2019 | Groetzbach et al. | |
| 2019/0167908 | A1 | 6/2019 | Fitzgibbon et al. | |
| 2019/0201634 | A1 | 7/2019 | Newton et al. | |
| 2019/0209786 | A1 | 7/2019 | Tschirren et al. | |
| 2019/0240394 | A1 | 8/2019 | Horvath et al. | |
| 2019/0269856 | A1 | 9/2019 | Baumeyer et al. | |
| 2020/0009323 | A1 | 1/2020 | Nair et al. | |
| 2020/0030539 | A1 | 1/2020 | Shabudin, Jr. | |
| 2020/0030547 | A1 | 1/2020 | Wang et al. | |
| 2020/0033069 | A1 | 1/2020 | Nakamura et al. | |
| 2020/0035047 | A1 | 1/2020 | Arnold | |
| 2020/0046910 | A1 | 2/2020 | Maxfield et al. | |
| 2020/0061309 | A1 | 2/2020 | Alexandersson | |
| 2020/0139046 | A1 | 5/2020 | Jacobsen | |
| 2020/0147311 | A1 | 5/2020 | Dugand et al. | |
| 2020/0164138 | A1 | 5/2020 | Holmqvist | |
| 2020/0254181 | A1 | 8/2020 | Mosebach et al. | |
| 2020/0289740 | A1 | 9/2020 | Tamtoro et al. | |
| 2020/0330699 | A1 | 10/2020 | Burren et al. | |
| 2021/0015741 | A1 | 1/2021 | Wotton et al. | |
| 2021/0085884 | A1 | 3/2021 | Liniger et al. | |
| 2021/0093790 | A1 | 4/2021 | Mosebach et al. | |
| 2021/0106756 | A1 | 4/2021 | Alexandersson | |
| 2021/0268201 | A1 | 9/2021 | Boström | |
| 2021/0275750 | A1 | 9/2021 | Helmer et al. | |
| 2022/0016359 | A1 | 1/2022 | Alexandersson | |

FOREIGN PATENT DOCUMENTS

| | | | |
|---|---|---|---|
| EP | 2323717 | B1 | 5/2013 |
| EP | 2525845 | B1 | 8/2014 |
| EP | 2588168 | B1 | 3/2015 |
| EP | 2731653 | B1 | 10/2015 |
| EP | 2931338 | B1 | 11/2016 |
| EP | 3235530 | A1 | 10/2017 |
| EP | 3320932 | A1 | 5/2018 |
| EP | 3107605 | B1 | 9/2018 |
| EP | 2654854 | B1 | 10/2018 |
| EP | 1850892 | B1 | 1/2019 |
| EP | 3541453 | A0 | 9/2019 |
| EP | 2953667 | B1 | 10/2019 |
| EP | 3407939 | B1 | 10/2019 |
| EP | 3490647 | B1 | 10/2021 |
| JP | 2013524459 | A | 6/2013 |
| JP | 2013534164 | A | 9/2013 |
| JP | 2015516845 | A | 6/2015 |
| JP | 2017525420 | A | 9/2017 |
| KR | 1020150097784 | A | 8/2015 |
| KR | 1020170048508 | A | 5/2017 |
| RU | 2671419 | C2 | 10/2018 |
| WO | 03041768 | A1 | 5/2003 |
| WO | 2003047663 | A3 | 6/2003 |
| WO | 2004098687 | A1 | 11/2004 |
| WO | 2005097238 | A3 | 10/2005 |
| WO | 2008059233 | A1 | 5/2008 |
| WO | 2009019436 | A1 | 2/2009 |
| WO | 2009019437 | A1 | 2/2009 |
| WO | 2009019438 | A1 | 2/2009 |
| WO | 2009019439 | A1 | 2/2009 |
| WO | 2009019440 | A1 | 2/2009 |
| WO | 2009081103 | A1 | 7/2009 |
| WO | 2009090499 | A2 | 7/2009 |
| WO | 2009143255 | A1 | 11/2009 |
| WO | 2012045350 | A1 | 4/2012 |
| WO | 2012164397 | A1 | 12/2012 |
| WO | 2013006119 | A1 | 1/2013 |
| WO | 2013152323 | A1 | 10/2013 |
| WO | 2015132234 | A1 | 9/2015 |
| WO | 2016193344 | A1 | 12/2016 |
| WO | 2016193346 | A1 | 12/2016 |
| WO | 2017089269 | A1 | 6/2017 |
| WO | 2017187177 | A1 | 11/2017 |

(56) References Cited

FOREIGN PATENT DOCUMENTS

| | | | |
|---|---|---|---|
| WO | 2017223354 | A1 | 12/2017 |
| WO | 2018004842 | A1 | 1/2018 |
| WO | 2018010947 | A1 | 1/2018 |
| WO | 2018018164 | A1 | 2/2018 |
| WO | 2018018165 | A1 | 2/2018 |
| WO | 2018018167 | A1 | 2/2018 |
| WO | 2018037034 | A1 | 3/2018 |
| WO | 2018053657 | A1 | 3/2018 |
| WO | 2018060745 | A1 | 4/2018 |
| WO | 2018069031 | A1 | 4/2018 |
| WO | 2018082886 | A1 | 5/2018 |
| WO | 2018091262 | A1 | 5/2018 |
| WO | 2018167640 | A1 | 9/2018 |
| WO | 2018172223 | A1 | 9/2018 |
| WO | 2018178127 | A8 | 10/2018 |
| WO | 2018192750 | A1 | 10/2018 |
| WO | 2018197774 | A1 | 11/2018 |
| WO | 2018206583 | A1 | 11/2018 |
| WO | 2018215271 | A1 | 11/2018 |
| WO | 2018226565 | A1 | 12/2018 |
| WO | 2020015986 | A1 | 1/2020 |

* cited by examiner

AUTO-INJECTOR WITH AUDIO INDICATOR

CROSS-REFERENCE TO RELATED APPLICATIONS

This application is the United States national phase of International Application No. PCT/EP2020/055006 filed Feb. 26, 2020, and claims priority to Europe patent Application No. 19305224.8 filed Feb. 26, 2019, the entire disclosures of which are hereby incorporated by reference in their entirety.

BACKGROUND OF THE INVENTION

Field of the Disclosure

The present disclosure relates generally to a drug delivery device and, more specifically, to an auto-injector.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. Many of these devices, such as auto-injectors, are designed so that the reservoir, such as a pre-filled syringe, is assembled into the device during assembly of the device. In addition to automatically deploying the needle-injection mechanism, many drug delivery devices also automatically shield the needle after use of the device to prevent any unintended contact with the needle.

SUMMARY OF THE INVENTION

In one aspect, a drug delivery device includes a housing, a syringe assembly including a barrel, a stopper, and a cannula, with at least a portion of the syringe assembly positioned within the housing, and a drive assembly including a plunger body configured to move the stopper within the barrel upon actuation of the drive assembly, with at least a portion of the drive assembly positioned within the housing. The plunger body has a pre-use position prior to movement of the plunger body, an injection position where the plunger body moves the stopper within the barrel, and a post-use position where movement of the plunger body has stopped. The device further includes an audio indicator member configured to provide an audible indication of a transition of the plunger body from the injection position to the post-use position.

The audio indicator member may have a biased position where the audio indicator member engages a portion of the housing and a released position, with the audio indicator positioned in the biased position when the plunger body is in the injection position and the audio indicator positioned in the released position when the plunger body is in the post-use position. Movement of the audio indicator from the biased position to the released position may cause the audible indication. The audio indicator member may be positioned in an unbiased position when the plunger body is in the pre-use position. The audio indicator member may engage a portion of the housing to provide the audible indication. The housing may include a lower housing shell, an upper housing shell, and a cassette body received by the lower housing shell, with the lower housing shell including an indicator platform and the audio indicator member engaging the indicator platform to provide the audible indication.

The housing may include a rib extending in a longitudinal direction of the device, with the audio indicator member engaging the rib to move the audio indicator member from the unbiased position to the biased position and the audio indicator member disengaging from the rib to move the audio indicator member from the biased position to the released position to cause the audible indication. The cassette body may include the rib. The rib may include a sloped surface configured to transition the audio indicator member from the unbiased position to the biased position. The rib may extend only a portion of a length of the cassette body. The audio indicator member may be formed integrally with the plunger body.

The device may further include a visual indicator member configured to provide a visual indication of a transition of the plunger body from the injection position to the post-use position. The visual indicator member may be visible via an indicator opening defined by the housing when the plunger body is in the post-use position. The housing may include a lower housing shell, with the lower housing shell defining the indicator opening. The visual indicator member may be formed integrally with the plunger body, with the visual indicator member spaced from the audio indicator member.

The drive assembly may further include a drive member configured to bias the plunger body from the pre-use position, to the injection position, and to the post-use position. The device may further include a needle cover having a pre-use position where the cannula is positioned within the needle cover, an actuation position where the needle cover is configured to actuate the drive assembly, and a post-use position where the cannula is positioned within the needle cover. The device may further include a lever actuation member moveable between a locked position where actuation of the drive assembly is prevented and a released position where actuation of the drive assembly is allowed, with the needle cover engaging the lever actuation member and moving the lever actuation member to the released position when the needle cover is in the actuation position.

The device may further include a syringe holder moveable relative to the housing, with the syringe assembly received by the syringe holder. The audio actuator member may be configured to restrict movement of the syringe holder when the plunger body is in the pre-use position.

The device may include one or several of the following features, taken individually or according to all technical possible combinations:

- a drug delivery device may comprise: a housing; a syringe assembly comprising a barrel, a stopper, and a cannula, at least a portion of the syringe assembly positioned within the housing; a drive assembly comprising a plunger body configured to move the stopper within the barrel upon actuation of the drive assembly, at least a portion of the drive assembly positioned within the housing, the plunger body having a pre-use position prior to movement of the plunger body, an injection position where the plunger body moves the stopper within the barrel, and a post-use position where movement of the plunger body has stopped; an audio indicator member configured to provide an audible indication of a transition of the plunger body from the injection position to the post-use position;
- the audio indicator member may have a biased position where the audio indicator member engages a portion of the housing and a released position, the audio indicator positioned in the biased position when the plunger body is in the injection position, the audio indicator positioned in the released position when the plunger body is in the post-use position, and wherein movement of the audio indicator from the biased position to the released position causes the audible indication;

the audio indicator member may be positioned in an unbiased position when the plunger body is in the pre-use position;

the audio indicator member may engage a portion of the housing to provide the audible indication;

the housing may comprise a lower housing shell, an upper housing shell, and a cassette body received by the lower housing shell, the lower housing shell comprises an indicator platform, the audio indicator member engaging the indicator platform to provide the audible indication;

the housing may comprise a rib extending in a longitudinal direction of the device, the audio indicator member engaging the rib to move the audio indicator member from the unbiased position to the biased position, the audio indicator member disengaging from the rib to move the audio indicator member from the biased position to the released position to cause the audible indication;

the housing may comprise a lower housing shell, an upper housing shell, and a cassette body received by the lower housing shell, the cassette body including the rib;

the rib may comprise a sloped surface configured to transition the audio indicator member from the unbiased position to the biased position;

the rib may extend only a portion of a length of the cassette body;

the audio indicator member may be formed integrally with the plunger body;

the drug delivery device may comprise a visual indicator member configured to provide a visual indication of a transition of the plunger body from the injection position to the post-use position;

the visual indicator member may be visible via an indicator opening defined by the housing when the plunger body is in the post-use position;

the housing may comprise a lower housing shell, the lower housing shell defining the indicator opening;

the visual indicator member may be formed integrally with the plunger body, the visual indicator member spaced from the audio indicator member;

the drug delivery device may comprise a syringe holder moveable relative to the housing, wherein the audio actuator member is configured to restrict movement of the syringe holder when the plunger body is in the pre-use position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1A:
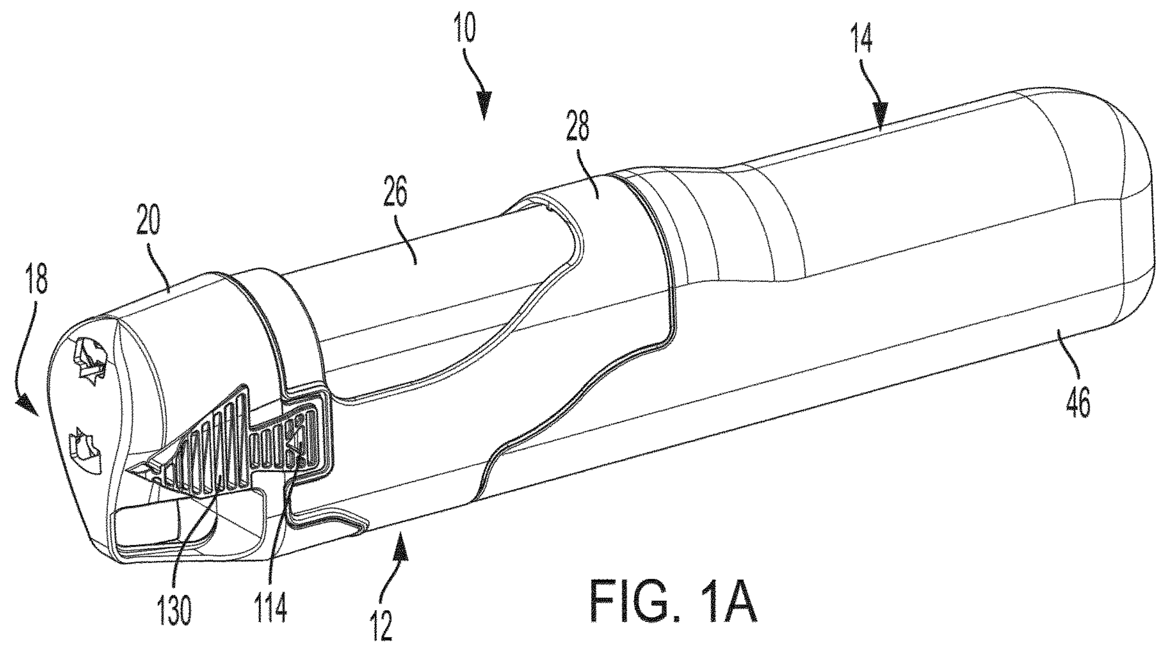
FIG. 1A is a perspective view of a drug delivery device according to one aspect of the present application, showing a storage position of the device.
Figure 1B:
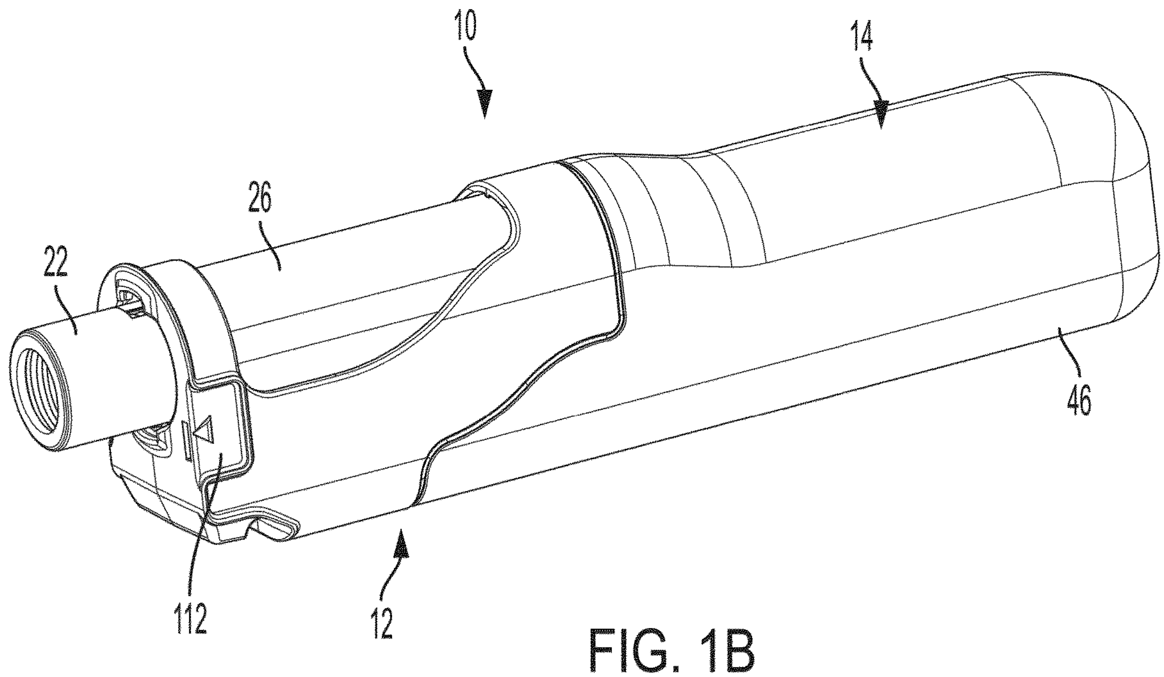
FIG. 1B is a perspective view of the drug delivery device of FIG. 1, showing a pre-use position of the device.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1A-10 a drug delivery device 10 according to one aspect of the present invention includes a first subassembly 12, a second subassembly 14, and a syringe assembly 16. The first subassembly 12 includes a cap 18 having an outer portion 20, a needle cover 22, a syringe holder 24, a cassette body 26, and a lower housing shell 28. The second subassembly 14 includes a drive assembly 40, a motor body 42, a lever actuation member 44, and an upper housing shell 46. The syringe assembly 16 is received by the syringe holder 24 and includes a barrel 52, a stopper 54, a cannula 56, and a rigid needle shield (RNS) 58. Although an RNS is utilized, other suitable needle shield arrangements may be utilized. The lower housing shell 28, the cassette body 26, and the upper housing shell 46 generally form a housing for receiving the various components of the device 10, although other suitable housing arrangements may be utilized. As discussed in more detail below, the first subassembly 12 and the second subassembly 14 are secured to each other during assembly by a locking clip 64, although other suitable arrangements may be utilized. The drug delivery device 10 may be an auto-injector, although the features described herein may be incorporated into other suitable drug delivery devices.

Figure 7:
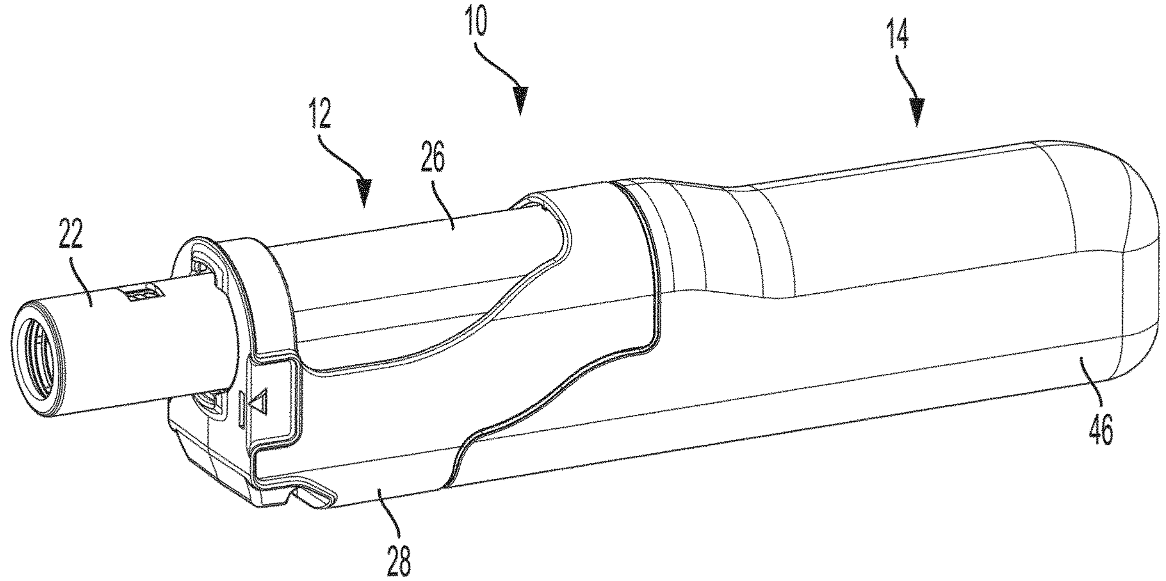
FIG. 7 is a perspective view of the drug delivery device of FIG. 1, showing a post-use position of the device.
Figure 8:
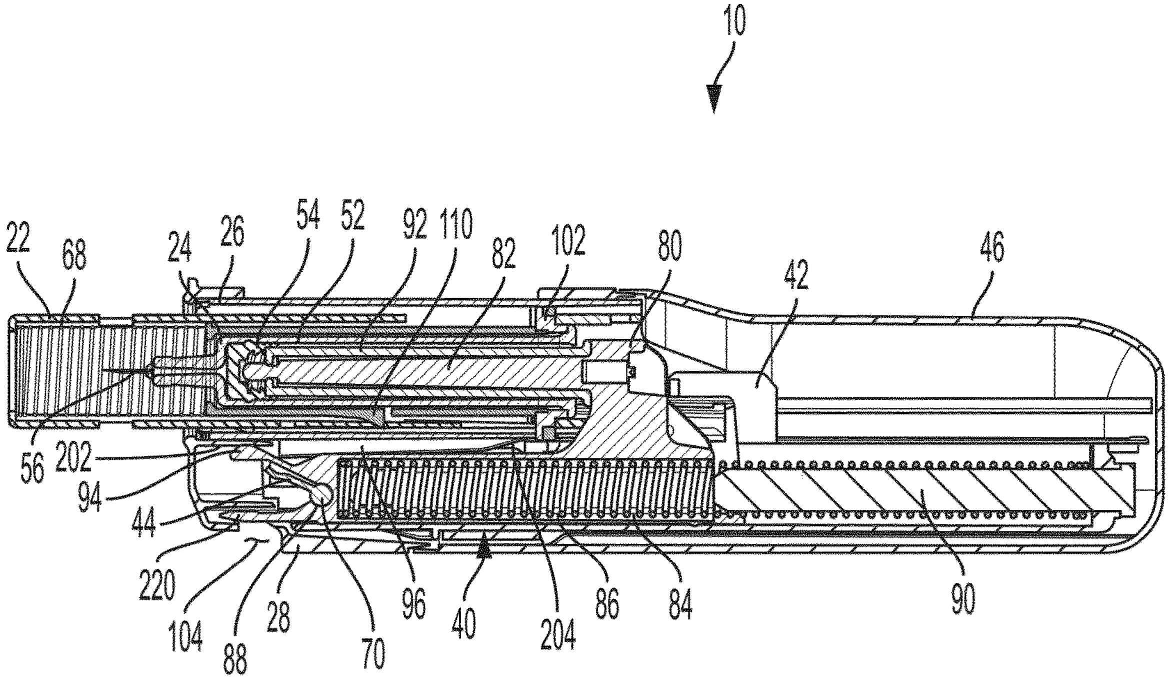
FIG. 8 is a cross-sectional view of the drug delivery device of FIG. 1, showing a post-use position of the device.
Figure 9:
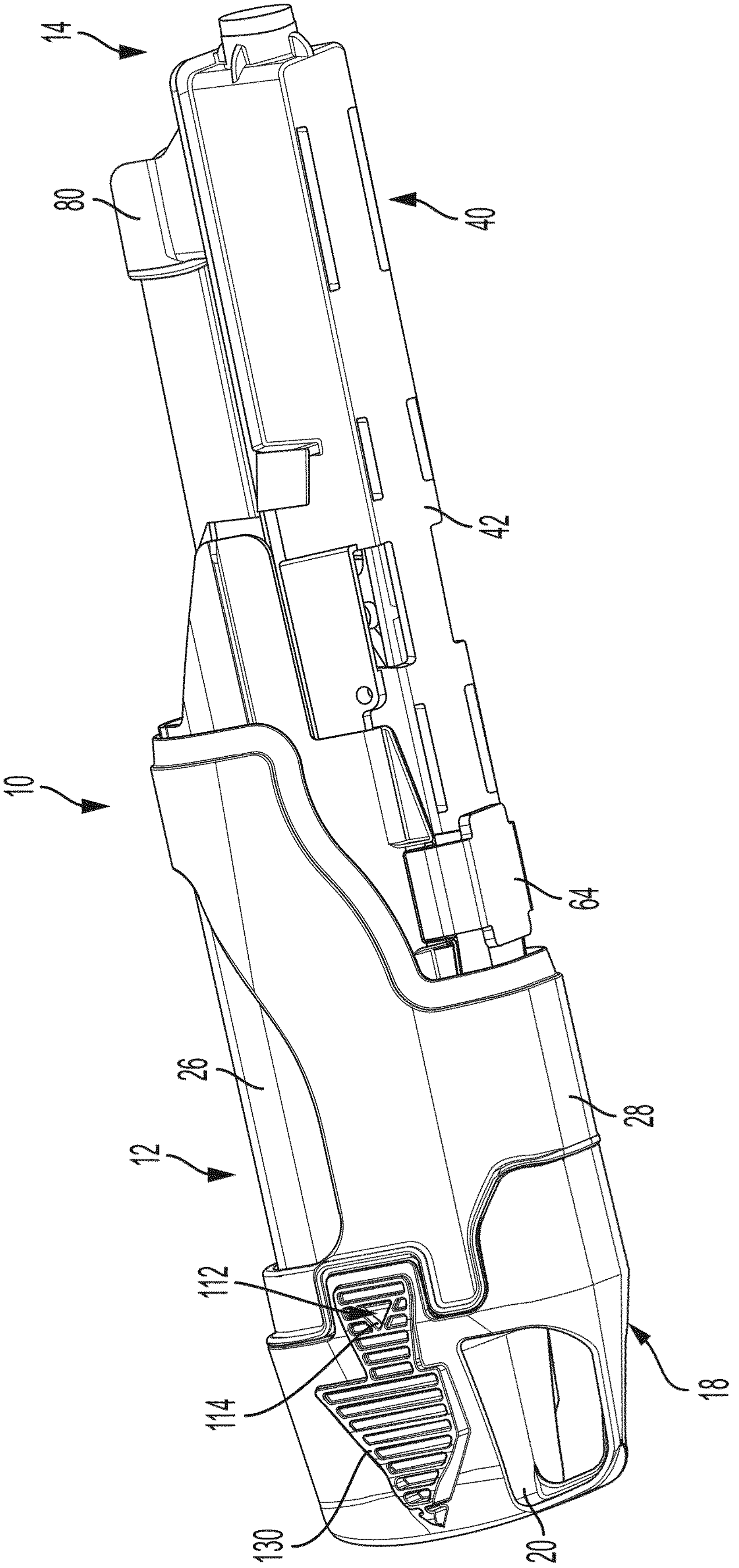
FIG. 9 is a perspective view of the drug delivery device of FIG. 1, showing a locking clip.
Figure 10:
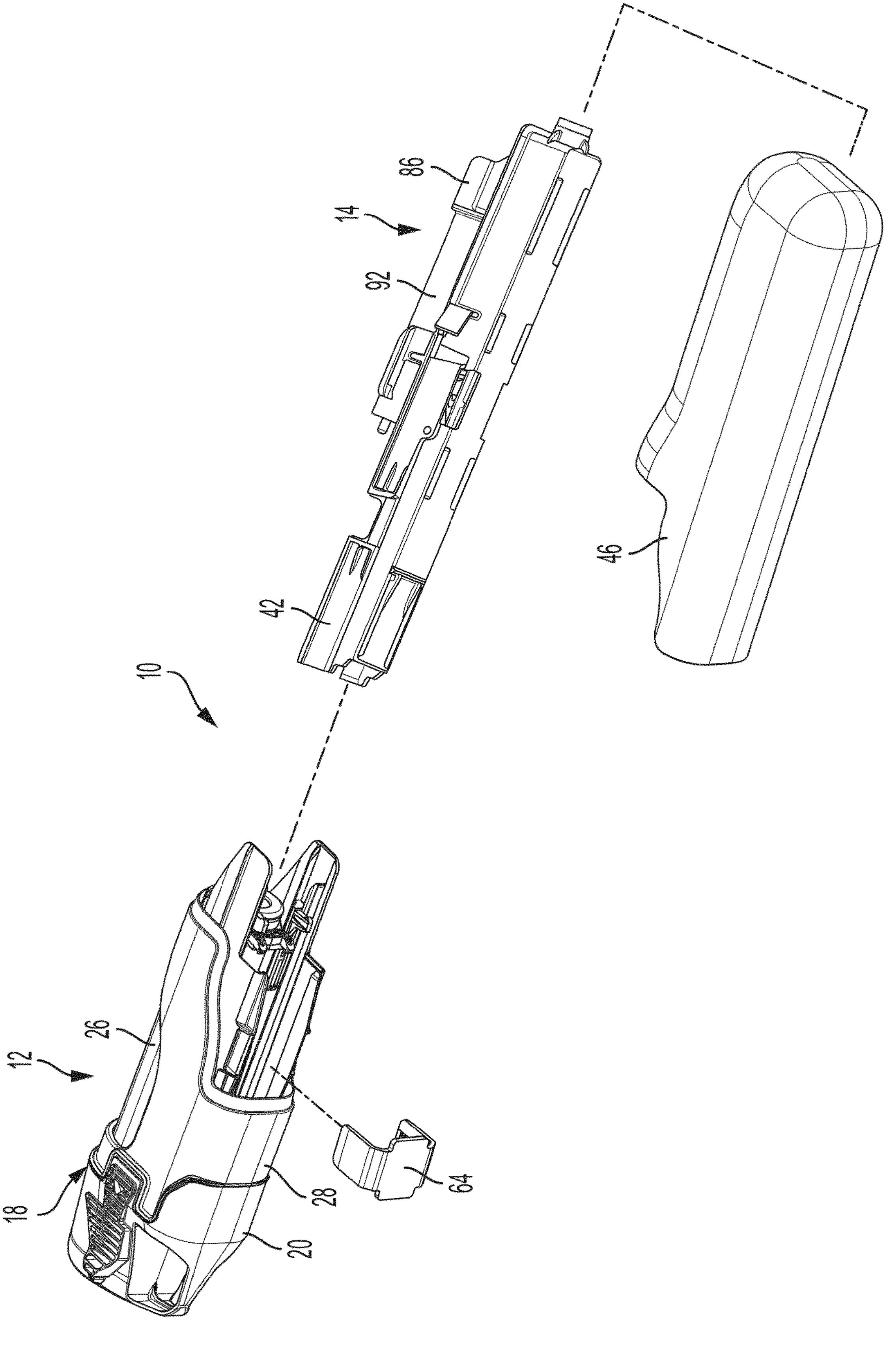
FIG. 10 is an exploded perspective view of the drug delivery device of FIG. 1, showing a locking clip.
Figure 11A:
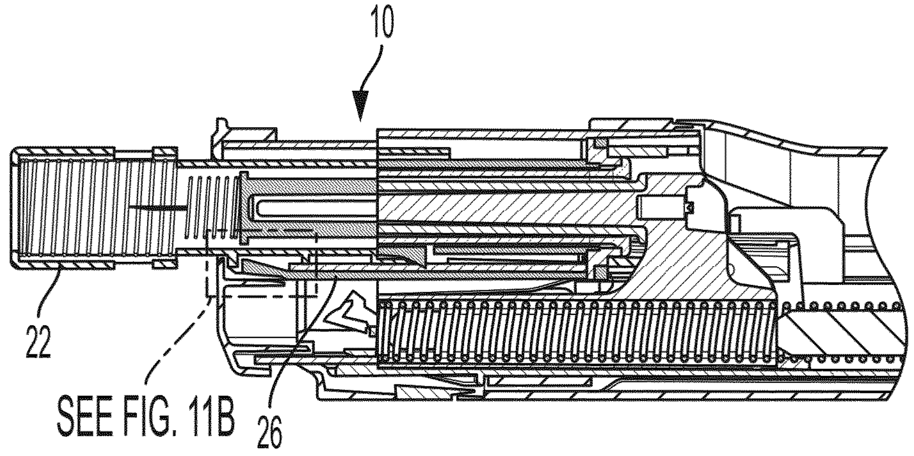
FIG. 11A is a partial cross-sectional view of the drug delivery device of FIG. 1, showing a lock arm of a cassette body.
Figure 11B:
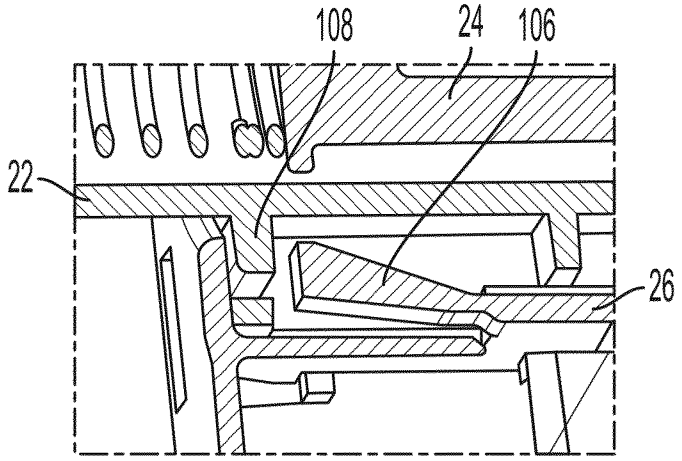
FIG. 11B is an enlarged cross-sectional view of the area indicated in FIG. 11A.

The drug delivery device 10 is configured to automatically deliver a dose of medicament from the syringe assembly 16 to a patient upon actuation of the device 10. More specifically, upon actuation of the drug delivery device 10, the drive assembly 40 is configured to engage the stopper 54 of the syringe assembly 16, displace the syringe assembly 16 such that the cannula 56 pierces the skin of the patient, and displace the stopper 54 within the barrel 52 of the syringe assembly 16 to deliver the medicament within the barrel 52. The drug delivery device 10 includes a storage position (FIGS. 1A and 2A), a pre-use position (FIGS. 1B and 2B), an actuation position (FIGS. 3 and 4), an injection position (FIGS. 5 and 6), and a post-use position (FIGS. 7 and 8). As discussed in more detail below, the needle cover 22 is configured to shield the cannula 56 of the syringe assembly 16 from the patient when the device 10 is in the pre-use and the post-use positions. In particular, the needle cover 22 is moveable between a pre-use position, an actuation position, and a post-use positon, with a spring 68 biasing the needle cover 22 towards the pre-use position and the post-use position. The spring 68 is positioned between the needle cover 22 and the syringe holder 24, although other suitable arrangements may be utilized. The lever actuation member 44 is moveable between a locked position where movement of the drive assembly 40 is prevented and a released position where movement of the drive assembly 40 is allowed. More specifically, the lever actuation member 44 is rotatable about a rotation axis 70 between the locked position and the released position. When the lever actuation member 44 is in the locked position, the lever actuation member 44 is engaged with the motor body 42 and the drive assembly 40 to prevent movement of the drive assembly 40. When the lever actuation member 44 is in the released position, the lever actuation member 44 is disengaged from the motor body 42 thereby allowing movement of the drive assembly 40 toward the syringe assembly 16. The rotation axis 70 of the lever actuation member 44 extends perpendicular to a longitudinal axis of the device 10, although other suitable arrangements may be utilized.

Referring again to FIGS. 1-10, the drive assembly 40 includes a plunger body 80 having a plunger rod portion 82 and a drive member 84. The plunger body 80 has a pre-use position (FIG. 2B) prior to movement of the plunger body 80, an injection position (FIG. 6) where the plunger body 80 moves the stopper 54 within the barrel 52, and a post-use position (FIG. 8) where movement of the plunger body 80 has stopped. The drive member 84 is a compression spring received within a drive opening 86 defined by the plunger body 80, although other suitable drive members may be utilized, including, but not limited to, compressed gas, an electric motor, hydraulic pressure, other types of springs, etc. The drive member 84 engages the plunger body 80 and the motor body 42 and biases the plunger body 80 in a direction extending from the second subassembly 14 toward the first subassembly 12. The plunger body 80 defines a lever opening 88 that receives the lever actuation member 44 and defines the rotation axis 70 of the lever actuation member

44. The lever actuation member 44 prevents movement of the plunger body 80 when the lever actuation member 44 is in the locked position through engagement of the lever actuation member 44 with the motor body 42. Upon rotation of the lever actuation member 44 from the locked position to the released position, the lever actuation member 44 is disengaged from the motor body 42 thereby allowing the drive member 84 to move the plunger body 80 and the plunger rod portion 82 toward the first subassembly 12. The plunger rod portion 82 and the drive member 84 are spaced from and parallel to each other and extend in a longitudinal direction of the device 10.

The drive assembly 40 further includes a spring guide member 90 secured to the upper housing shell 46 and received within the drive opening 86 of the plunger body 80. The drive member 84 is received by the spring guide member 90 such that the drive member 84 is positioned between the plunger body 80 and the spring guide member 90. The drive assembly 40 also includes a plunger rod cover 92 that receives the plunger rod portion 82 of the plunger body 80. The plunger rod cover 92 is configured to guide insertion of the plunger rod portion 82 into the barrel 52 of the syringe assembly 16 and engage the stopper 54 of the syringe assembly 16 to dispense the medicament from the barrel 52 of the syringe assembly 16. The plunger rod cover 92 and the plunger rod portion 82 may be two separate parts or may be formed integrally as a single piece.

The plunger body 80 of the drive assembly 40 also includes an audio indicator member 94 configured to provide an audible indication to a user when the device 10 transitions to the post-use position. As discussed in more detail below, the audio indicator member 94 is configured to engage one or more ribs 96 of the cassette body 26 when the device 10 is in the injection position thereby deflecting the audio indicator member 94. When the drug delivery device 10 transitions from the injection position to the post-use position, the audio indicator member 94 disengages from the rib(s) 96 of the cassette body 26 and contacts the lower housing shell 28 to provide an audible click, although the audio indicator member 94 could also contact other suitable portions of the device 10 to provide the audible indicator.

Figure 2A:
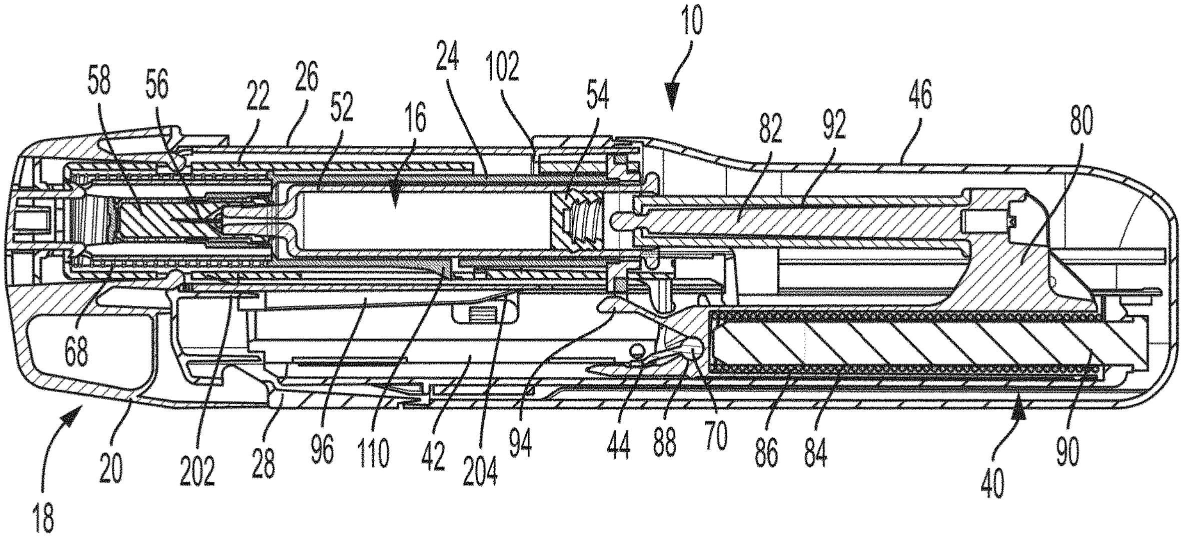
FIG. 2A is a cross-sectional view of the drug delivery device of FIG. 1, showing a storage position of the device.
Figure 2B:
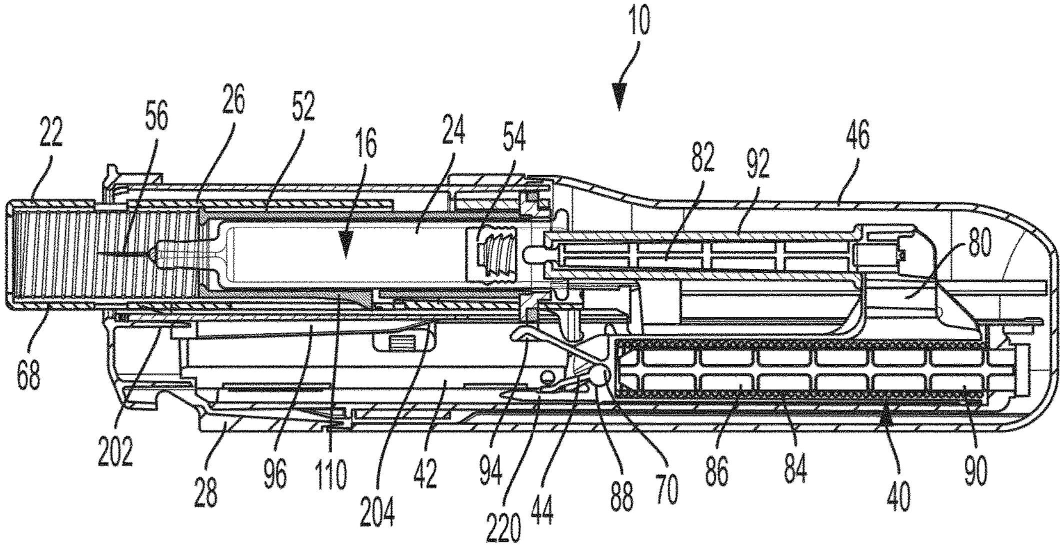
FIG. 2B is a cross-sectional view of the drug delivery device of FIG. 1, showing a pre use position of the device.

Referring to FIGS. 1A-2B, in the storage position, the cap 18 is secured to the lower housing shell 28 and engaged with the needle cover 22. Movement of the needle cover 22 from the pre-use position to the actuation position causes engagement between the needle cover 22 and the lever actuation member 44 thereby actuating the drive assembly 40. After removal of the cap 18 by grasping the outer portion 20, the needle cover 22 may be moved from the pre-use position to the actuation position by pressing the needle cover 22 against a skin surface of a patient and axially pressing the device 10 against the skin surface. As detailed below, the engagement between the cap 18 and the needle cover 22 prevents the needle cover 22 from moving into engagement with the lever actuation member 44. Accordingly, removal of the cap 18 from the device 10 allows for the actuation of the device 10. Removal of the cap 18 from the device 10, as shown in FIGS. 1B and 2B, also removes the RNS 58 from the syringe barrel 52 thereby exposing the cannula 56, which is still received within the needle cover 22 in the pre-use position of the device 10. The cap 18 may include one or more components received within the outer portion 20 to facilitate the removal of the RNS 58.

Figure 3:
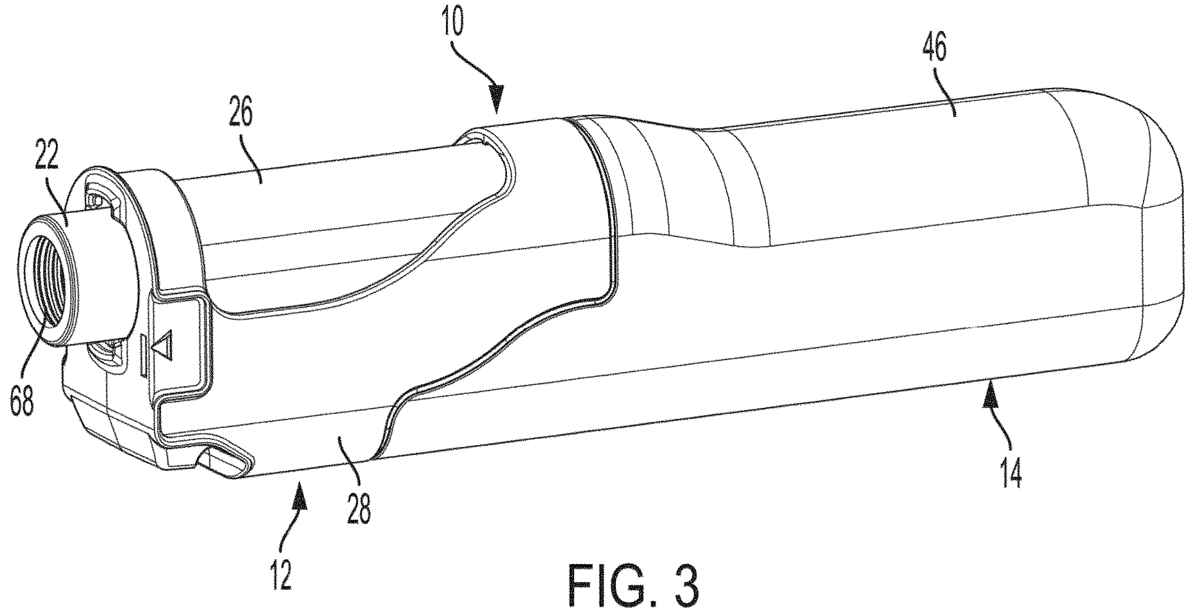
FIG. 3 is a perspective view of the drug delivery device of FIG. 1, showing an actuation position of the device.
Figure 4:
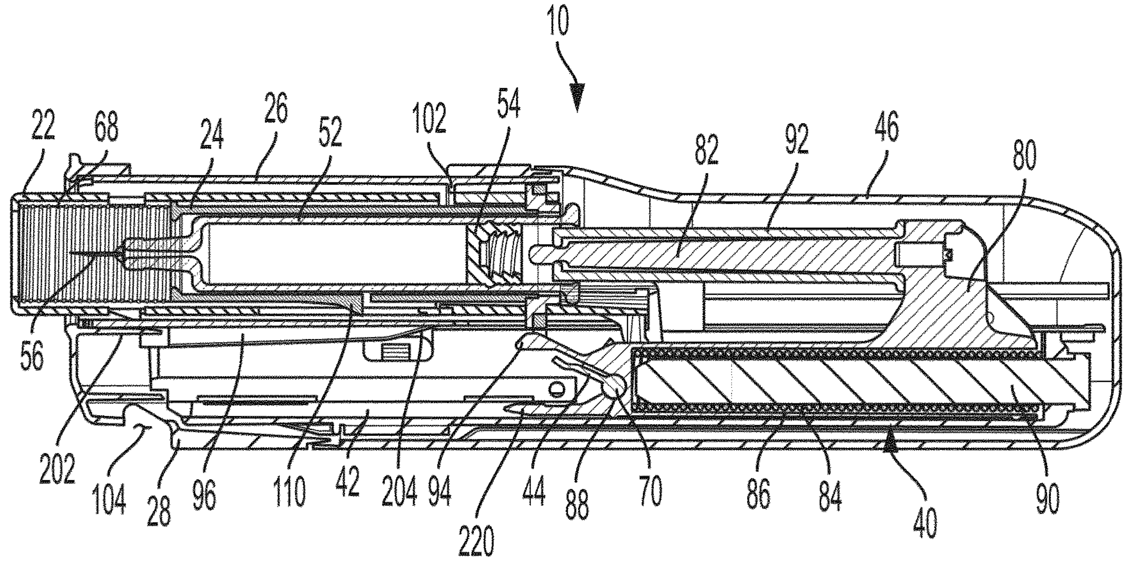
FIG. 4 is a cross-sectional view of the drug delivery device of FIG. 1, showing an actuation position of the device.

Referring to FIGS. 3 and 4, in the actuation position, the cap 18 is removed and the needle cover 22 is positioned in the actuation position by engaging a skin surface of a patient, which moves the needle cover 22 further within the device 10 toward the second subassembly 14. When the needle cover 22 has moved a sufficient distance within the device 10, a portion of the needle cover 22 engages the lever actuation member 44, which rotates the lever actuation member 44 about the rotation axis 70 from the locked position to the released position.

Figure 5:
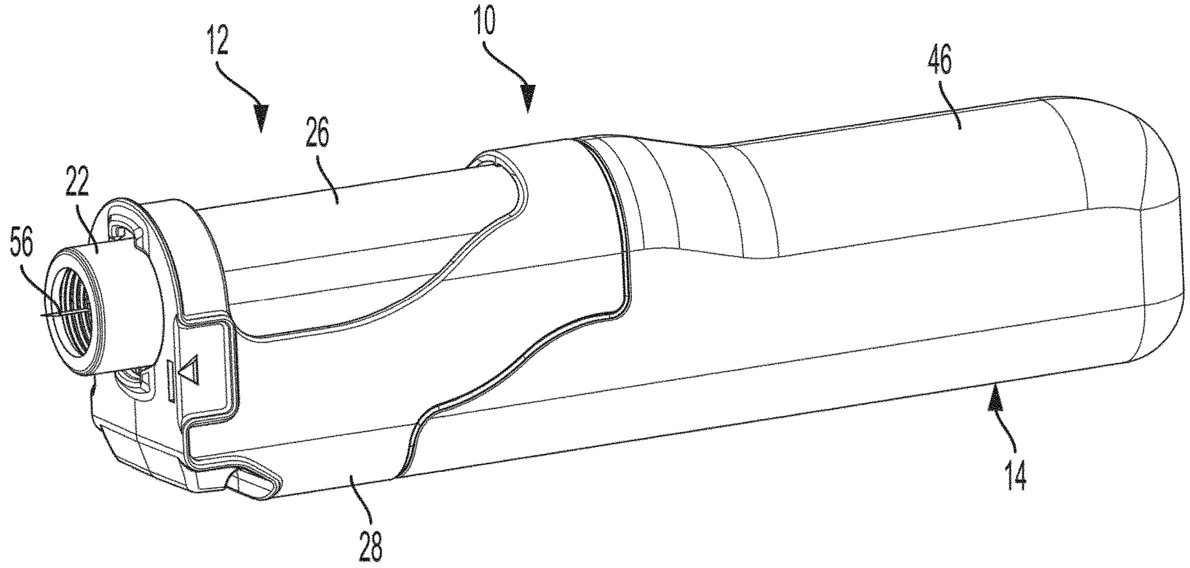
FIG. 5 is a perspective view of the drug delivery device of FIG. 1, showing an injection position of the device.
Figure 6:
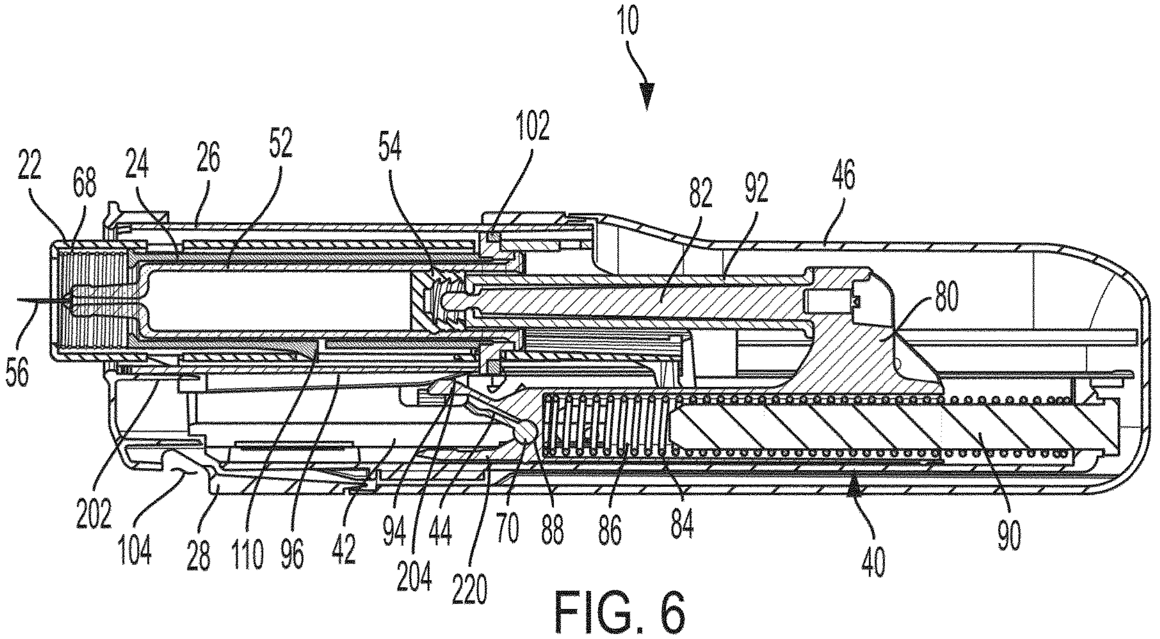
FIG. 6 is a cross-sectional view of the drug delivery device of FIG. 1, showing an injection position of the device.

Referring to FIGS. 5 and 6, in the injection position, the lever actuation member 44 is in the released position, which allows the plunger body 80 of the drive assembly 40 to move toward the first subassembly 12 such that the plunger body 80 or the plunger rod cover 92 engages the stopper of the syringe assembly 16. Initial engagement of the drive assembly 40 with the syringe assembly 16 moves the syringe assembly 16 and the syringe holder 24 within the device 10 and relative to the cassette body 26 until the syringe holder 24 abuts a stop 102 defined by the cassette body 26. During this initial movement of the syringe assembly 16 and syringe holder 24 with the needle cover 22 pressed against a skin surface of a patient, the cannula 56 of the syringe assembly 16 extends beyond the needle cover 22 and pierces the skin surface of the patient. Further movement of the plunger body 80, which is driven by the drive member 84, moves the stopper 54 relative to the barrel 52 of the syringe assembly 16 to dispense medicament from the barrel 52 of the syringe assembly 16, through the cannula 56, and into the patient. The plunger body 80 will continue moving until the stopper 54 bottoms out on the barrel 52 of the syringe assembly 16. When the stopper 54 bottoms out or just before the stopper 54 bottoms out, the audio indicator member 94 will disengage from the rib(s) 96 of the cassette body 26 and contact the lower housing shell 28 at approximately the same time to provide the audible indication to the patient that the dose of medicament has been delivered. In addition to the audible indication, the drug delivery device 10 provides one or more visual indicators to notify a patient of the status of the device 10. In particular, the cassette body 26 may be formed from transparent material to allow visual confirmation of movement of the stopper 54 and/or another visual indicator provided by the drive assembly 40, syringe holder 24, and/or syringe assembly 16. The lower housing shell 28 also defines an indicator opening 104, which provides visual indication that the plunger body 80 is in a final position and the dose of medicament has been delivered. The visual indicators may utilize contrasting colors, symbols, patterns, or any other suitable visual indicia to indicate the various statuses of the device.

Figure 12:
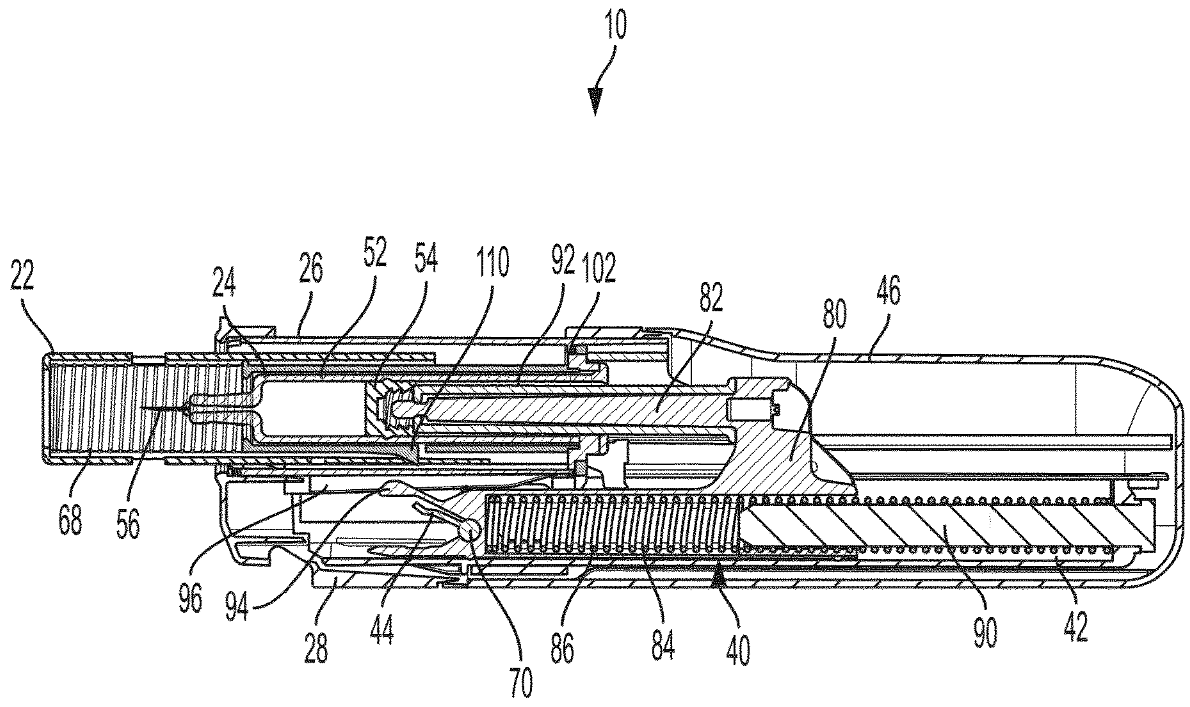
FIG. 12 is a cross-sectional view of the drug delivery device of FIG. 1, showing a post-use position of the device prior to full delivery of medicament.

Referring to FIGS. 7, 8, 11A, 11B, and 12, in the post-use position, the needle cover 22 extends to the post-use position to shield the cannula 56 when the needle cover 22 is removed from a skin surface of a patient. As shown more clearly in FIG. 11B, the cassette body 26 includes at least one lock arm 106 and the needle cover 22 includes at least one lock protrusion 108, although other suitable configurations may be utilized. The lock arm 106 of the cassette body 26 engages the lock protrusion 108 of the needle cover 22 to prevent any further use of the device 10 and exposing of the cannula 56 of the syringe assembly 16. During the transition of the device 10 from the injection position to the post-use position, the lock arm 106 of the cassette body 26 deflects to allow the lock protrusion 108 of the needle cover 22 to pass by the cassette body 26 with the lock arm 106 returning to its original position to prevent movement of the needle cover 22 back toward the pre-use and actuation positions. In the pre-use position of the needle cover 22, a portion of the needle cover 22 engages a cover stop 110 of the syringe holder 24 to limit axial movement of the needle cover 22 in a direction extending from the second subassembly 14 toward the first subassembly 12. After use of the device 10, the syringe holder 24 is displaced within the cassette body 26 relative to the needle cover 22, which allows the needle cover 22 to extend to the post-use position when a patient removes the needle cover 22 from a skin surface. As shown in FIG. 12, the needle cover 22 will move to the post-use position when the needle cover 22 is removed from a skin surface of a patient regardless of a position of the stopper 54 within the barrel 52 of the syringe assembly 16. Accordingly, if a patient removes the needle cover 22 from a skin surface after only a portion of the dose of medicament has been delivered, the needle cover 22 will still move to the post-use position and will prevent further use of the device 10.

Referring to FIGS. 1-8 and 12-16, as discussed above, the plunger body 80 of the drive assembly 40 includes the audio indicator member 94 configured to provide an audible indication of a transition of the plunger body 80 from the injection position to the post-use position. The audible indication may be a click, knock, ring, or any other suitable audible and/or tactile indication. The audio indicator member 94 has a biased position (FIG. 6) where the audio indicator member 94 engages a portion of the cassette body 26, an unbiased position (FIGS. 2B and 4), and a released position (FIG. 8), although the audio indicator member 94 could also engage other portions of the device 10 to bias the audio indicator member 94. The audio indicator 94 is positioned in the biased position when the plunger body 80 is in the injection position (FIG. 6) and is positioned in the released position when the plunger body 80 is in the post-use position (FIG. 8). Movement of the audio indicator member 94 from the biased position to the released position causes the audible indication. As shown in FIG. 2B, the audio indicator member 94 is positioned in the unbiased position when the plunger body 80 is in the pre-use position.

As discussed above, the cassette body 26, the lower housing shell 28, and the upper housing shell 46 may form the housing for the device 10, with the upper housing shell 46 abutting the lower housing shell 28 and the lower housing shell 28 receiving the cassette body 26. The audio indicator member 94 engages a portion of the lower housing shell 28 to provide the audible indication. More specifically, as shown more clearly in FIG. 14, the lower housing shell 28 includes an indicator platform 202. The audio indicator member 94 engages the indicator platform 202 to provide the audible indication, although the audio indicator member 94 could also engage other portions of the device 10 to provide the audible indication.

Figure 15:
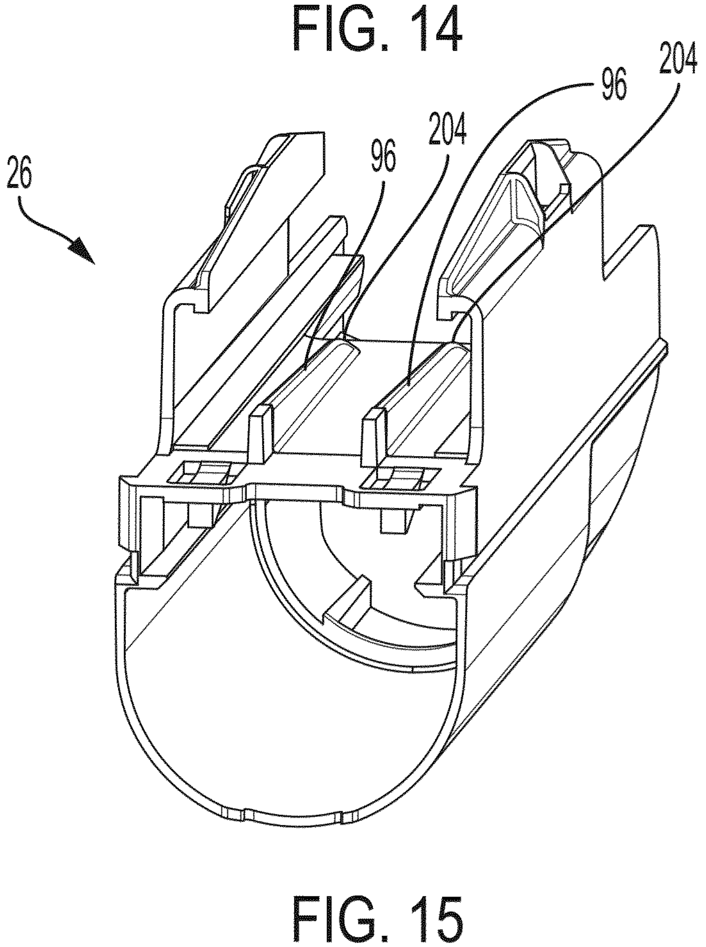
FIG. 15 is a perspective view of a cassette body of the drug delivery device of FIG. 1.
Figure 16:
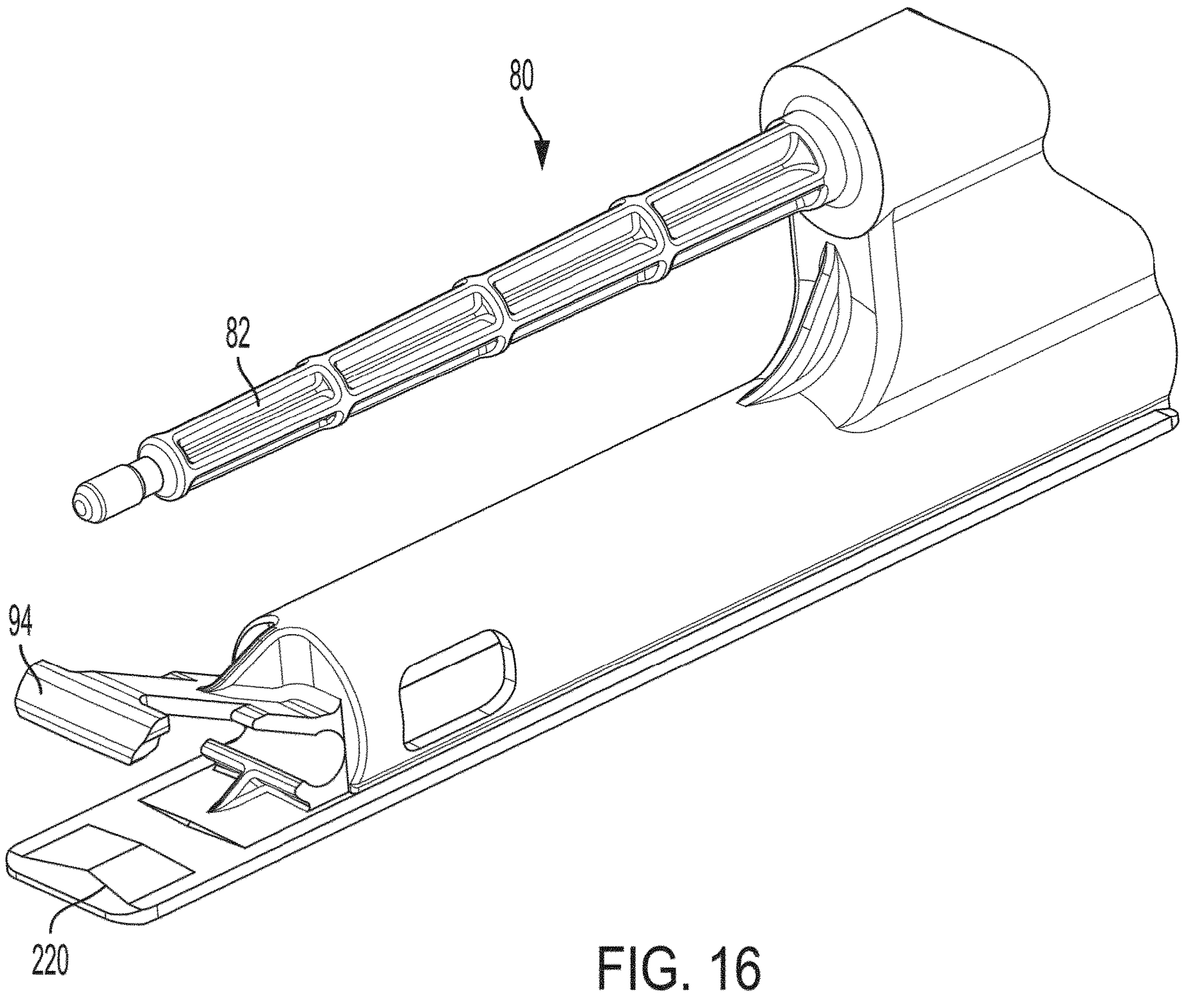
FIG. 16 is a perspective view of a plunger body of the drug delivery device of FIG. 1.
Figure 17:
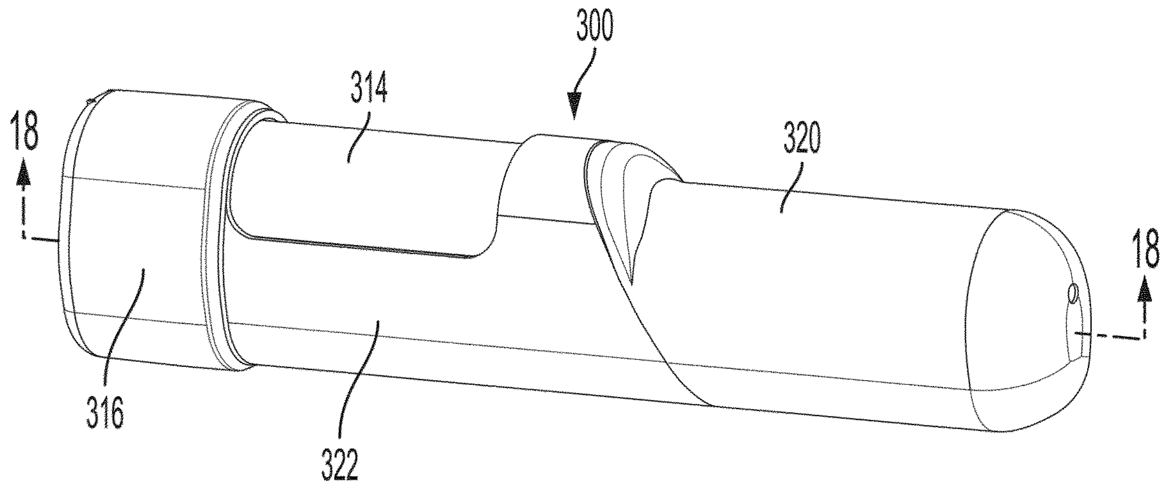
FIG. 17 is a perspective view of a drug delivery device according to a further aspect of the present application, showing a storage position of the device.
Figure 18:
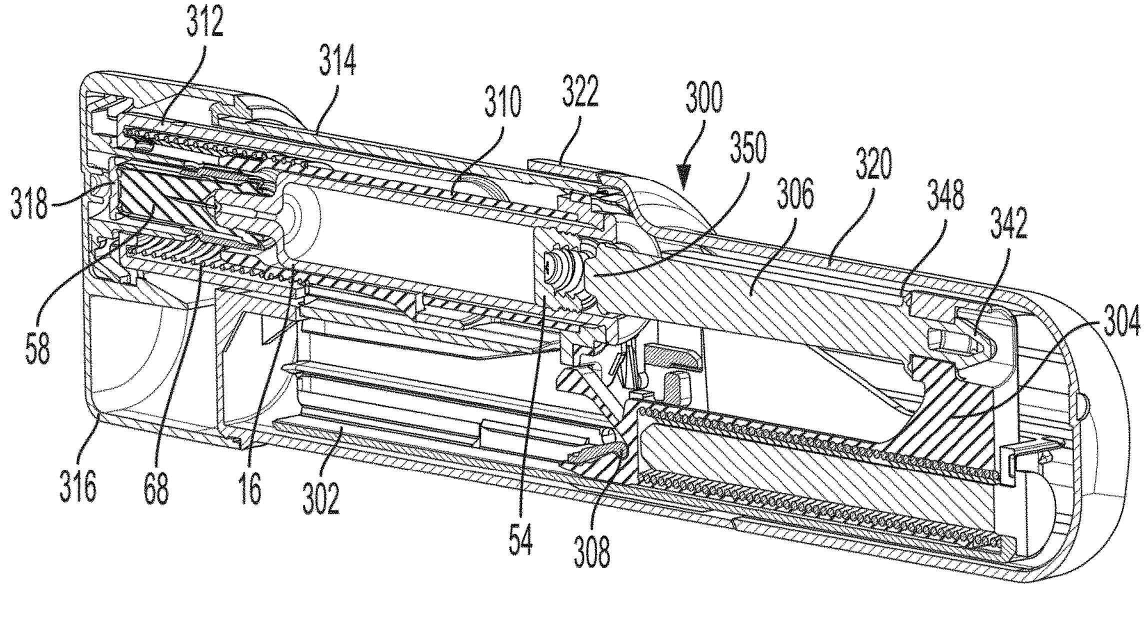
FIG. 18 is a cross-sectional view taken along line 18-18 shown in FIG. 17.
Figure 19:
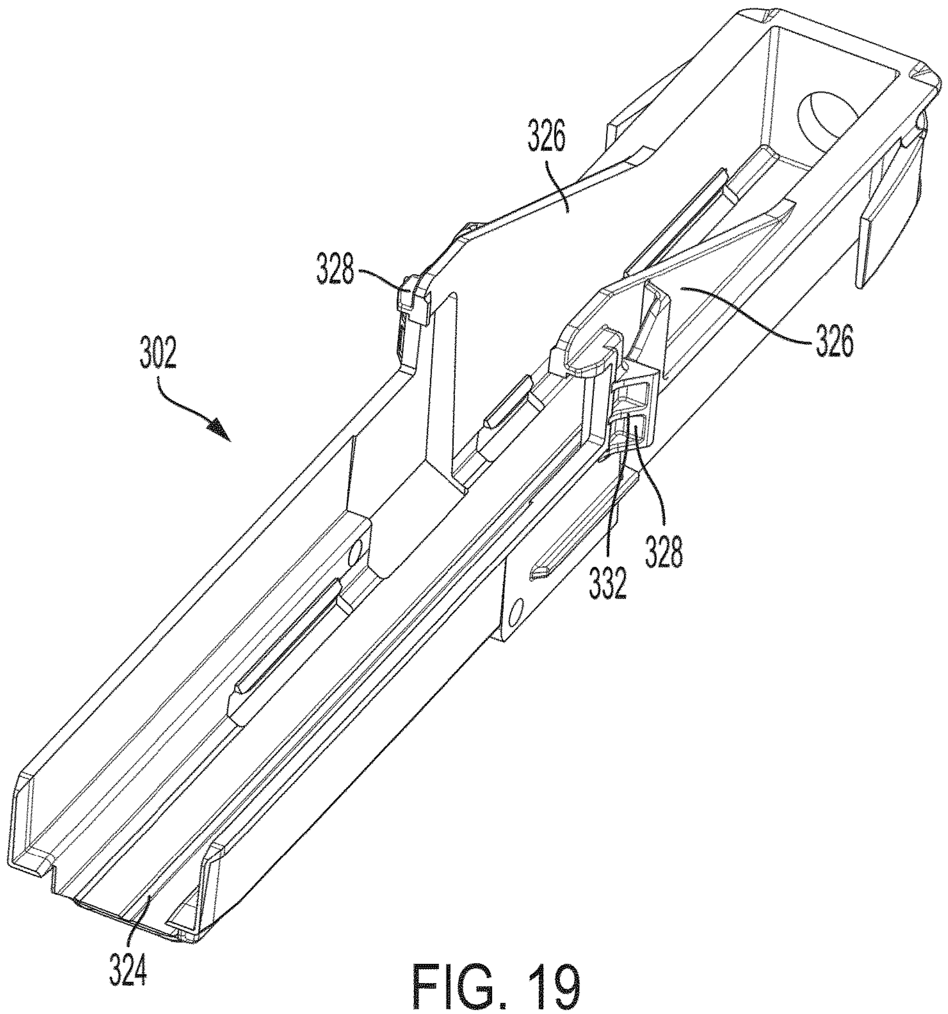
FIG. 19 is a top perspective view of a motor body of the drug delivery device of FIG. 17.
Figure 20:
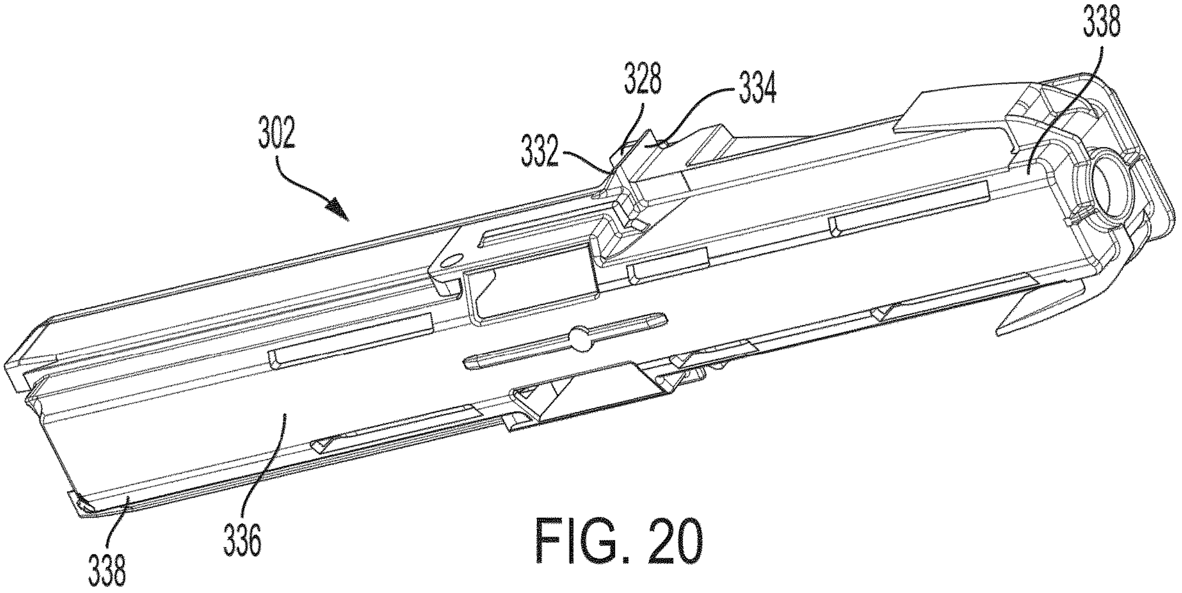
FIG. 20 is a bottom perspective view of the motor body of FIG. 19.
Figure 21:
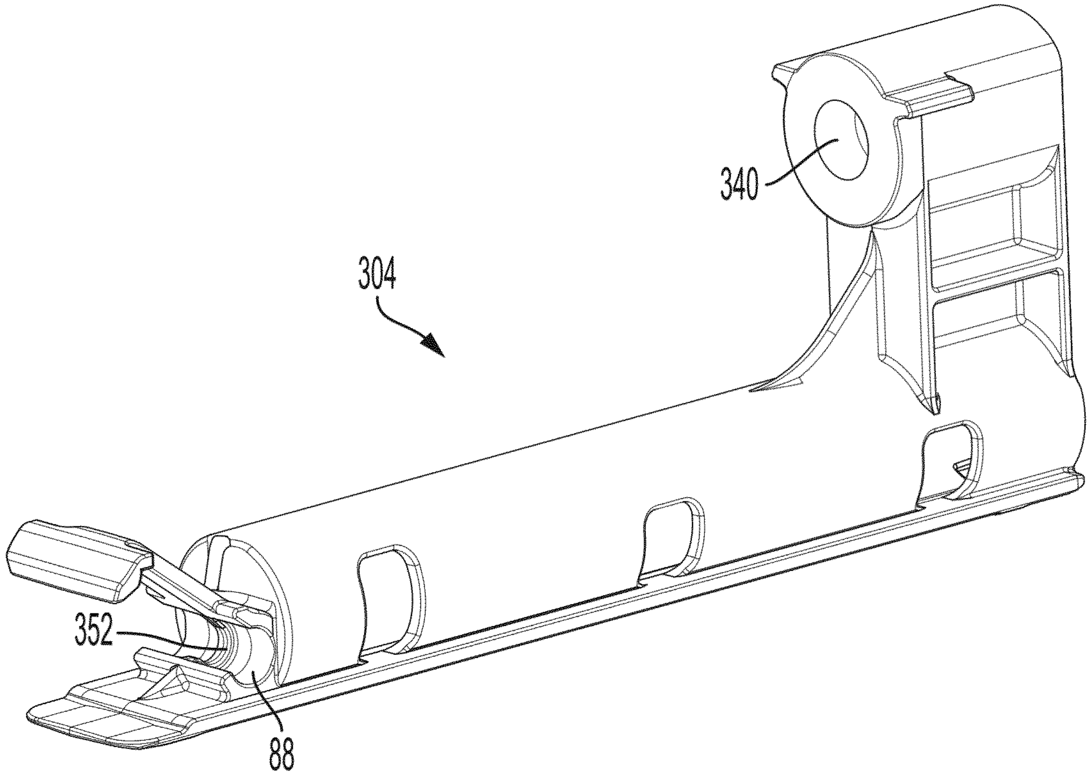
FIG. 21 is a front perspective view of a plunger body of the drug delivery device of FIG. 17.
Figure 22:
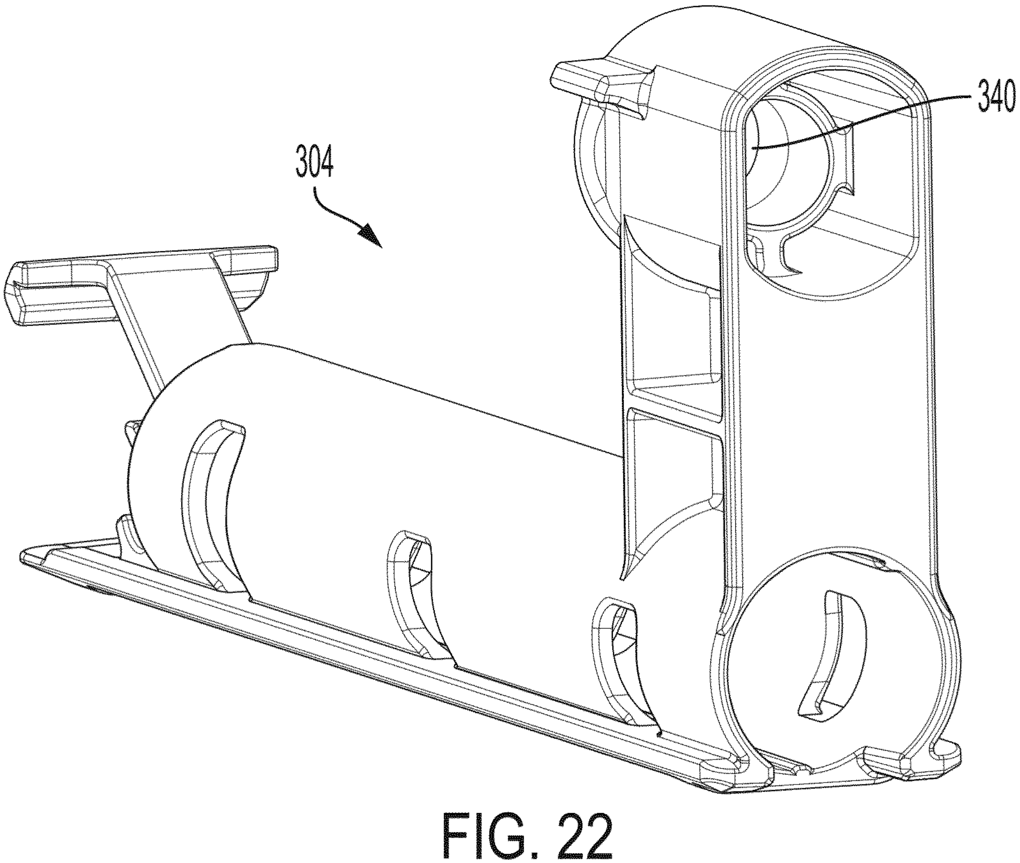
FIG. 22 is a rear perspective view of the plunger body of FIG. 21.
Figure 23:
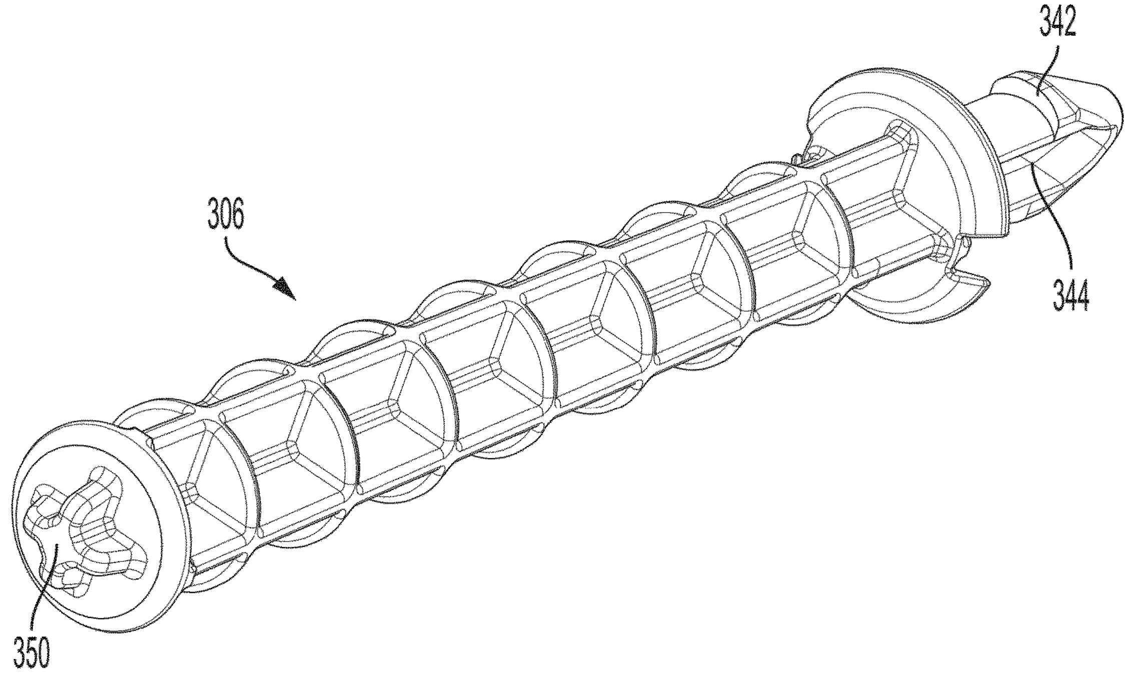
FIG. 23 is a front perspective view of a plunger rod portion of the drug delivery device of FIG. 17.
Figure 24:
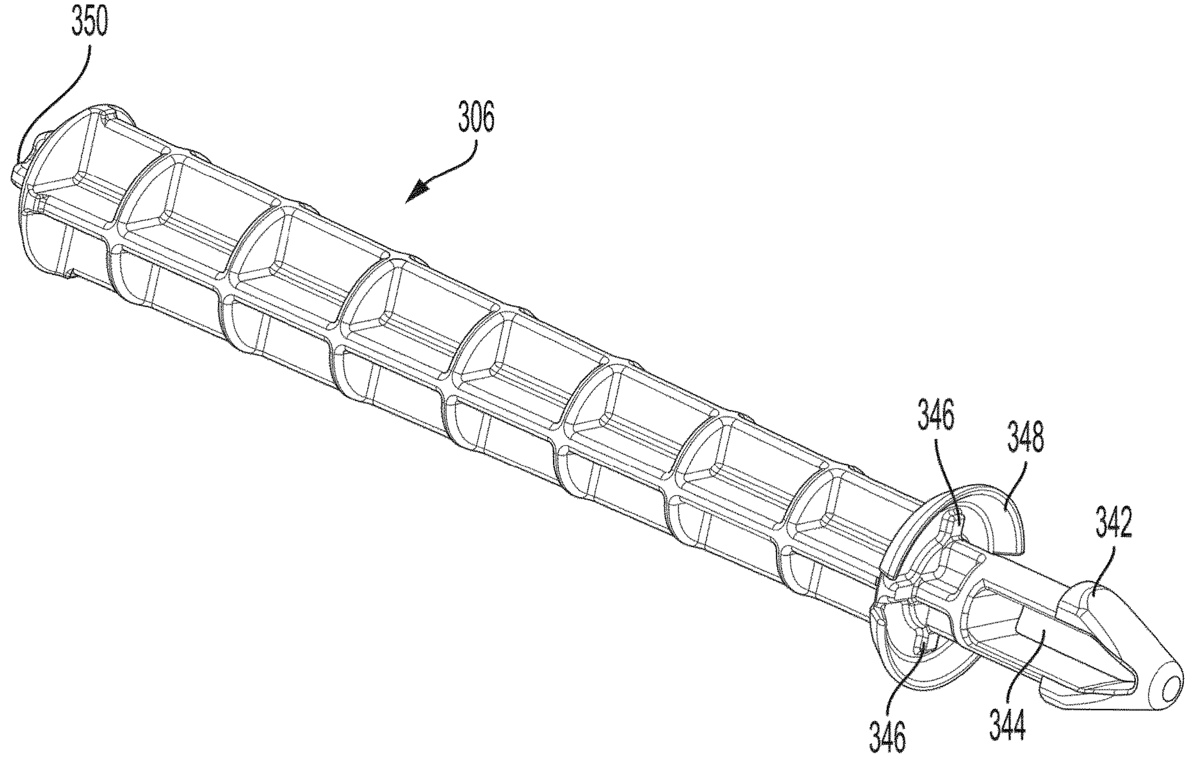
FIG. 24 is a rear perspective view of the plunger rod portion of FIG. 23.

Referring again to FIGS. 1-8 and 12-16, as discussed above, the cassette body 26 includes at least one rib 96 extending in a longitudinal direction of the device 10. As shown in FIG. 15, the cassette body 26 includes two ribs 96. The audio indicator member 94 engages the ribs 96 to move the audio indicator member 94 from the unbiased position to the biased position. The audio indicator member 94 disengages from the ribs 96 to move the audio indicator member 94 from the biased position to the released position to cause the audible indication. In particular, upon actuation of the device 10, the audio indicator member 94 moves from the unbiased position shown in FIG. 4 to the biased position shown in FIG. 6 as the plunger body 80 moves relative to the motor body 42 such that the audio indicator member 94 engages the ribs 96 and deflects the audio indicator member 94 thereby moving the audio indicator member 94 to the biased position. The audio indicator member 94 will continue to slide along the ribs 96 until the audio indicator member 94 reaches the end of the ribs 96. After disengaging from the ribs 96, the audio indicator member 94 transitions to the released position and contacts the indicator platform 202 to provide the audible indication. The audio indicator member 94 may provide the audible indication just before the stopper 54 bottoms out on the barrel 52, although the audio indicator member 94 may provide the audible indication at approximately the same time as the stopper 54 bottoming out or may delay the audible indication a predetermined time after completion of the delivery of the dose of medicament. The ribs 96 include a sloped surface 204 configured to transition the audio indicator member 94 from the unbiased position to the biased position. The sloped surface 204 provides a smooth transition from the unbiased position to the biased position. The ribs 96 only extend a portion of a length of the cassette body 26, although other suitable configurations may be utilized. The audio indicator member 94 is formed integrally with the plunger body 80 and moves with the plunger body 80, although the audio indicator member 94 may be formed separately from the plunger body 80.

Figure 13:
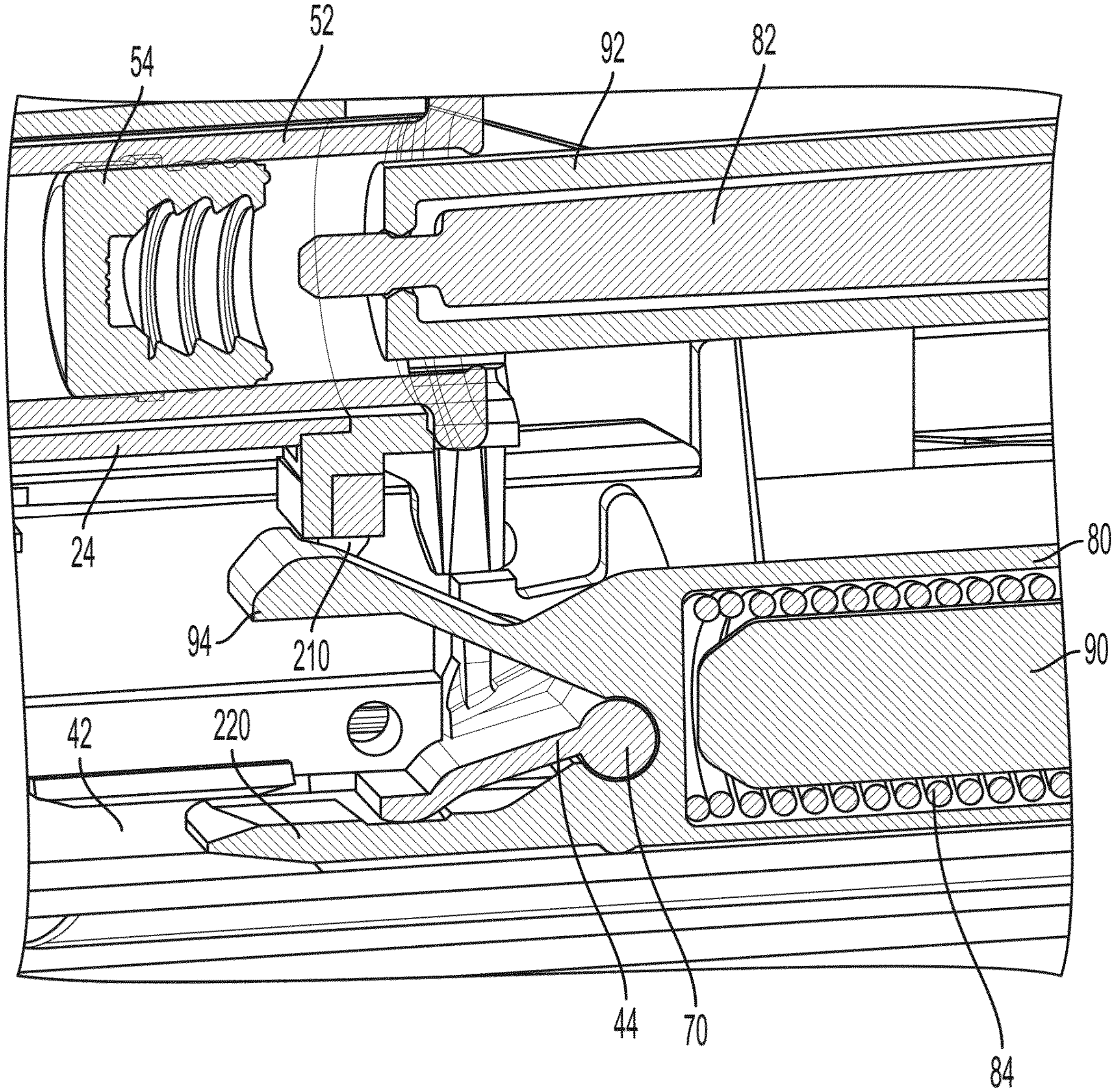
FIG. 13 is a partial cross-sectional view of the drug delivery device of FIG. 1, showing a storage position of the device.
Figure 14:
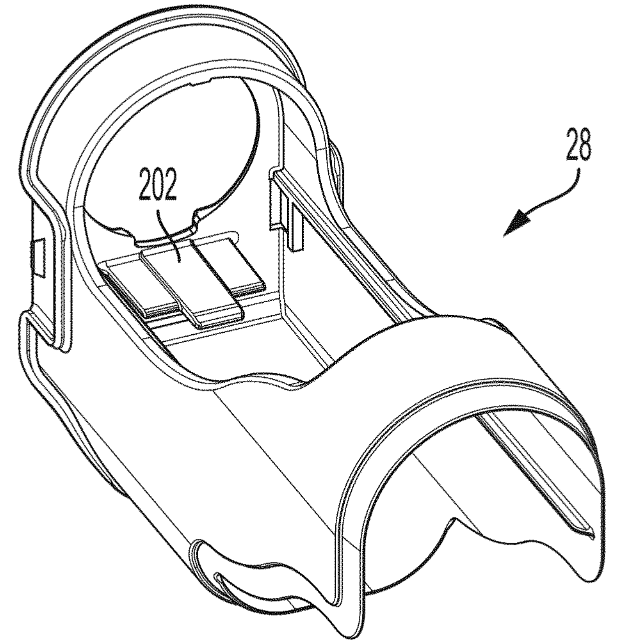
FIG. 14 is a perspective view of a lower housing shell of the drug delivery device of FIG. 1.

Referring to FIG. 13, the audio indicator member 94 is configured to restrict movement of the syringe holder 24 when the plunger body 80 is in the pre-use position. As discussed above, the lever actuation member 44 prevents movement of the plunger body 80. The syringe holder 24 is moveable relative to the cassette body 26. The audio indicator member 94 engages at least one arm 210 of the syringe holder 24 to prevent movement of the syringe holder 24 during movement of the device 10 in the pre-use position or during removal of the cap 18. The arm(s) 210 extend radially outward from the syringe holder 24 with a portion of the audio indicator member 94 positioned between the arm(s) 210 of the syringe holder 24 such that movement of the syringe holder 24 in a direction extending from the second subassembly 14 toward the first subassembly 12 causes at least one of the arm(s) 210 to engage the audio indicator member 94 to restrict any further movement of the syringe holder 24.

Referring to FIGS. 2B, 6, 8, and 16, as mentioned above, the device 10 also includes a visual indicator member 220 configured to provide a visual indication of a transition of the plunger body 80 from the injection position (FIG. 6) to the post-use position (FIG. 8). The visual indicator member 220 is visible via the indicator opening 104 defined by the lower housing shell 28. The visual indicator 220 member is formed integrally with the plunger body 80 and spaced from the audio indicator member 94, although other suitable configurations may be utilized. As noted above, the visual indicator member 220 may utilize contrasting colors, symbols, patterns, or any other suitable visual indicia to indicate the various statuses of the device.

Referring to FIGS. 17-41, a drug delivery device 300 according to a further aspect of the present invention is shown. The drug delivery device 300 is similar to the drug delivery device 10 shown in FIGS. 1A-16, with certain differences discussed below in detail. The drug delivery device 300 includes, among other components, a motor body 302, a plunger body 304, a plunger rod portion 306, a lever actuation member 308, a syringe holder 310, a needle cover 312, a cassette body 314, a cap 316, a retainer 318, an upper housing shell 320, and a lower housing shell 322.

Referring to FIGS. 17-20, the motor body 302 is similar and functions similarly to the motor body 42 of FIGS. 1A-16, but further includes a longitudinal groove 324, reinforcing rib(s) 326, and cassette clip(s) 328. The longitudinal groove 324 is configured to receive a molding split line of the plunger body 304 to ensure smooth sliding between the motor body 302 and the plunger body 304. The reinforcing rib(s) 326 provide additional support for the pair of arms 260 of the motor body 302. The cassette clip(s) 328 is received by an opening(s) 330 defined by the cassette body 314 to secure the motor body 302 to the cassette body 314, which is discussed in more detail below. The cassette clip(s) 328 include an angled face 332 and a planar face 334, which is configured to allow insertion of the cassette clip(s) 328 into the opening(s) 330 of the cassette body 314, but prevent the easy removal of the cassette clip(s) 328 once inserted into the opening(s) 330 of the cassette body 314. A bottom surface 336 of the motor body 302 includes chamfered portions 338 to aid assembly of the device 300.

Referring to FIGS. 18 and 21-24, the plunger body 304 is formed separately from the plunger rod portion 306 rather than being formed integrally. Further, the device 300 does not include the plunger rod cover 92. The plunger body 304 defines an opening 340 that receives a plunger rod clip 342 of the plunger rod portion 306. The plunger rod clip 342 is barb-shaped and configured to be inserted into the opening 340 of the plunger body 304, but not easily removed from the opening 340, although other suitable shapes and configurations may be utilized. The plunger rod clip 342 defines a central opening 344, which allows the plunger rod clip 342 to compress as the plunger rod clip 342 is inserted into the opening 340 of the plunger body 304 and expand to its original shape once received within the plunger body 304. The plunger rod portion 306 includes a plunger body stop(s) 346 and a biasing member 348. The plunger body stop(s) 346, which may be one or more projections, contact the plunger body 304 when the plunger rod clip 342 is inserted into the opening 340 of the plunger body 304. The biasing member 348 engages the plunger body 304 during insertion of the plunger rod clip 342 into the opening 340 of the plunger body 304 and biases the plunger rod portion 306 toward the plunger body 304. The biasing member 348 provides additional leeway for insertion of the plunger rod clip 342 into the opening 340 of the plunger body 304 while ensuring there is no gap between the plunger body 304 and the plunger rod portion 306 after assembly. The biasing member 348 of the plunger rod portion 306 is annular, although other suitable shapes and configurations may be utilized.

The plunger rod portion 306 further includes a stopper interface 350 that is received by the stopper 54. The stopper interface 350 is a cruciform projection, although other suitable shapes and configurations may be utilized. The plunger rod portion 306 has a conical external shape configured to reduce stress on the syringe assembly 16, although other suitable shapes may be utilized. The plunger body 304 includes a lever rib 352 extending into the lever opening 88 of the plunger body 304. The lever rib 352 is configured to be received by the lever actuation member 308, as discussed in more detail below.

Figure 25:
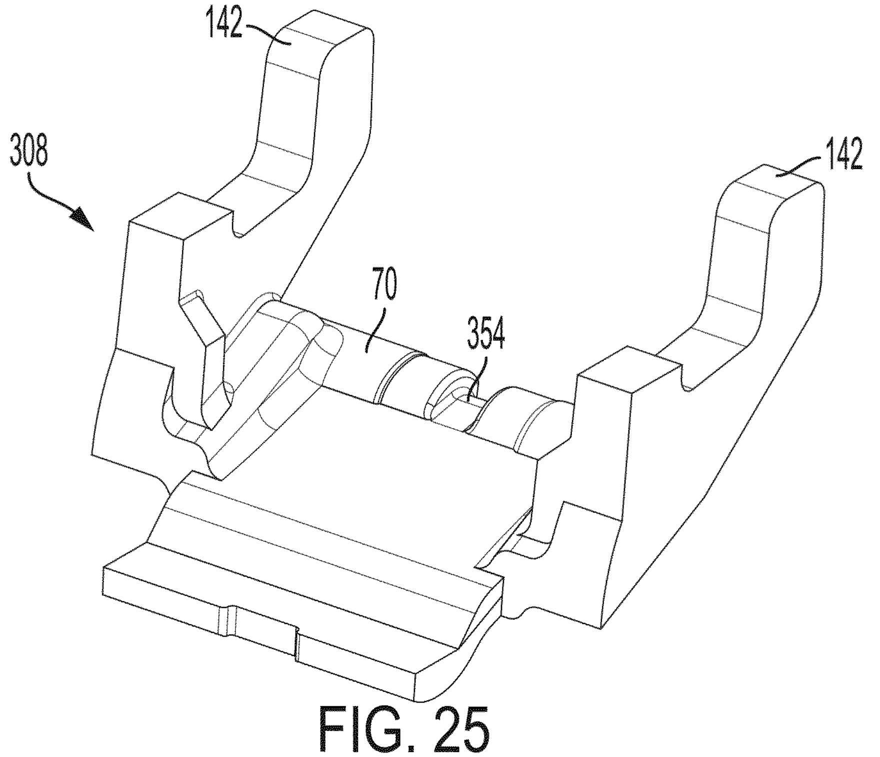
FIG. 25 is a top perspective view of a lever actuation member of the drug delivery device of FIG. 17.
Figure 26:
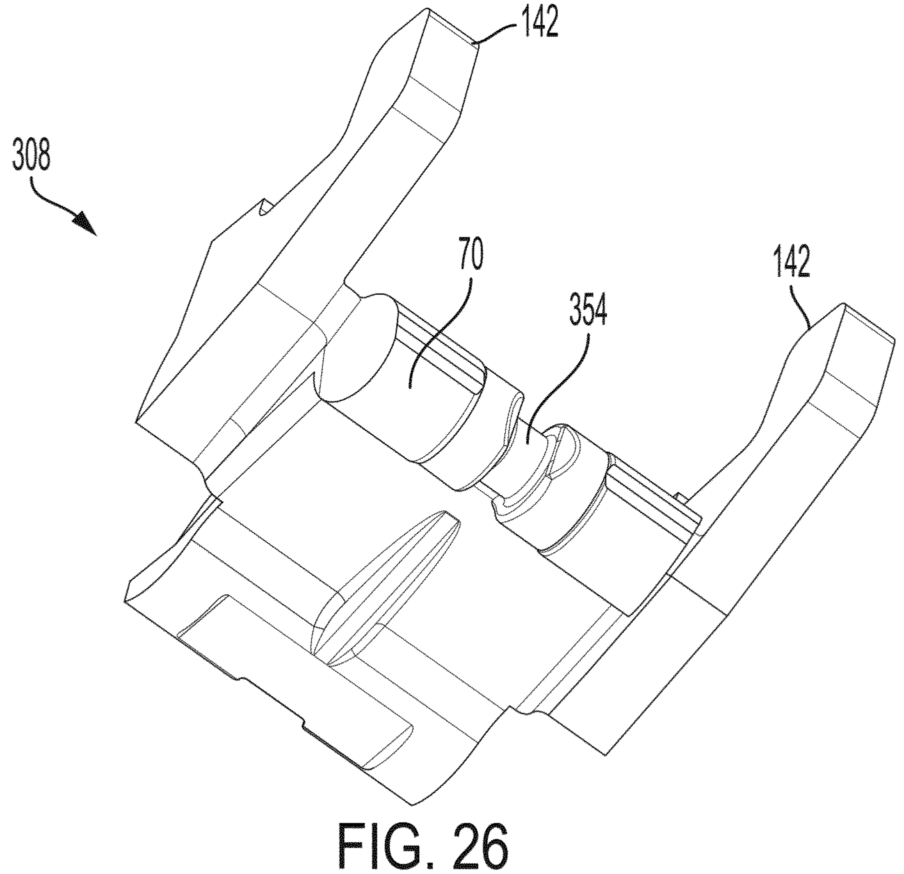
FIG. 26 is a bottom perspective view of the lever actuation member of the drug delivery device of FIG. 25.

Referring to FIGS. 25 and 26, the lever actuation member 308 is similar to and functions similarly to the lever actuation member 44 described above and shown in FIGS. 1A-16. The lever actuation member 308, however, defines a groove 354 at the rotation axis 70 that receives the lever rib 352 of the plunger body 304. The engagement between the groove 354 and the lever rib 352 prevents relative lateral movement between the plunger body 304 and the lever actuation member 308. The needle cover contact surface 142 of the lever actuation member 308 includes a larger surface compared to the needle cover contact surface 142 of the lever actuation member 44 of FIGS. 1A-16.

Figure 27:
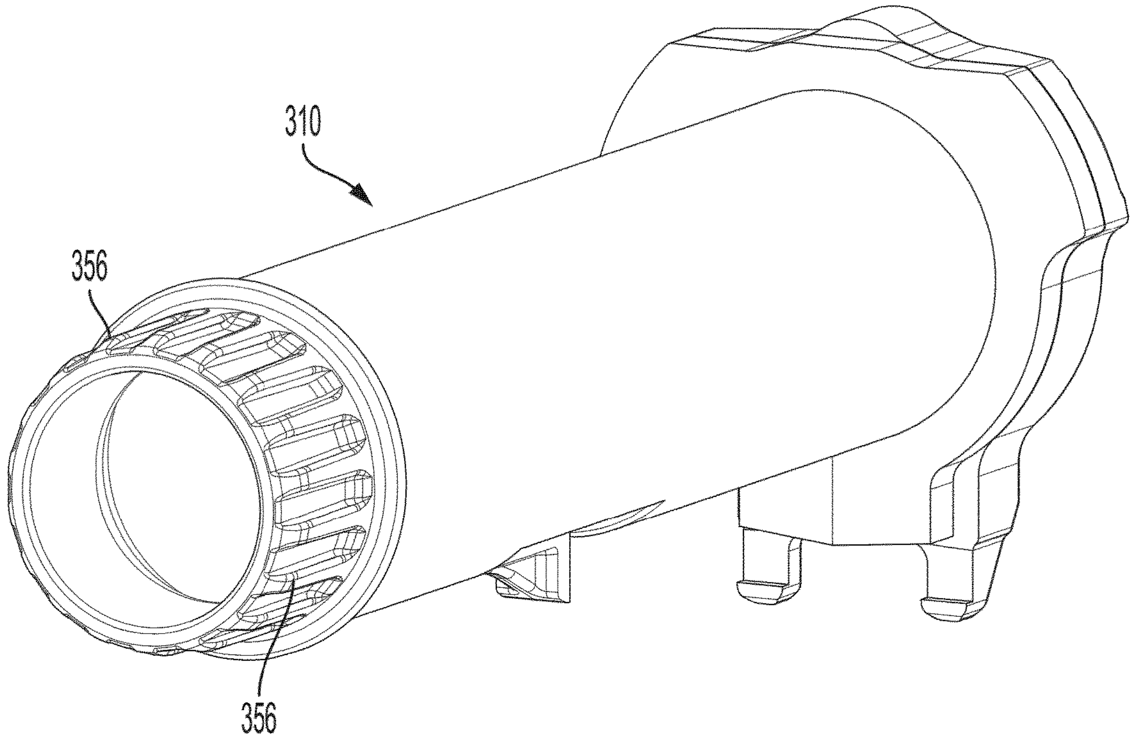
FIG. 27 is a front perspective view of a syringe holder of the drug delivery device of FIG. 17.
Figure 28:
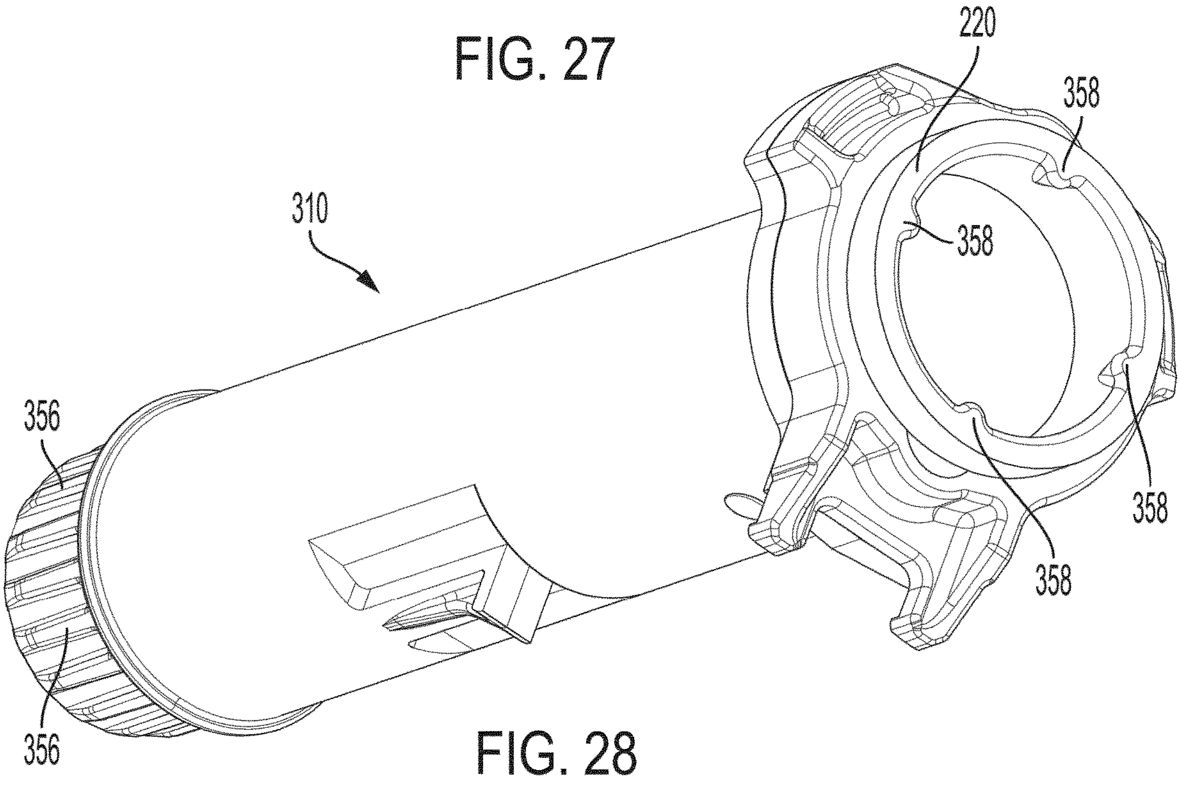
FIG. 28 is a rear perspective view of the syringe holder of the drug delivery device of FIG. 27.

Referring to FIGS. 27 and 28, the syringe holder 310 is similar to and functions similarly to the syringe holder 24 of FIGS. 1A-16. The syringe holder 310, however, further includes a plurality of ribs 356 extending circumferentially around the syringe holder 310. The plurality of ribs engage the spring 68. The securing ring 220 of the syringe holder 310 further includes a plurality of projections 358 that extend radially inward. The plurality of projections 358 engage the syringe assembly 16 to remove any gap between the outer surface of the syringe assembly 16 and the syringe holder 310. The plurality of projections 358 are elastomeric and may compress when the syringe assembly 16 is received within the syringe holder 310.

Figure 29:
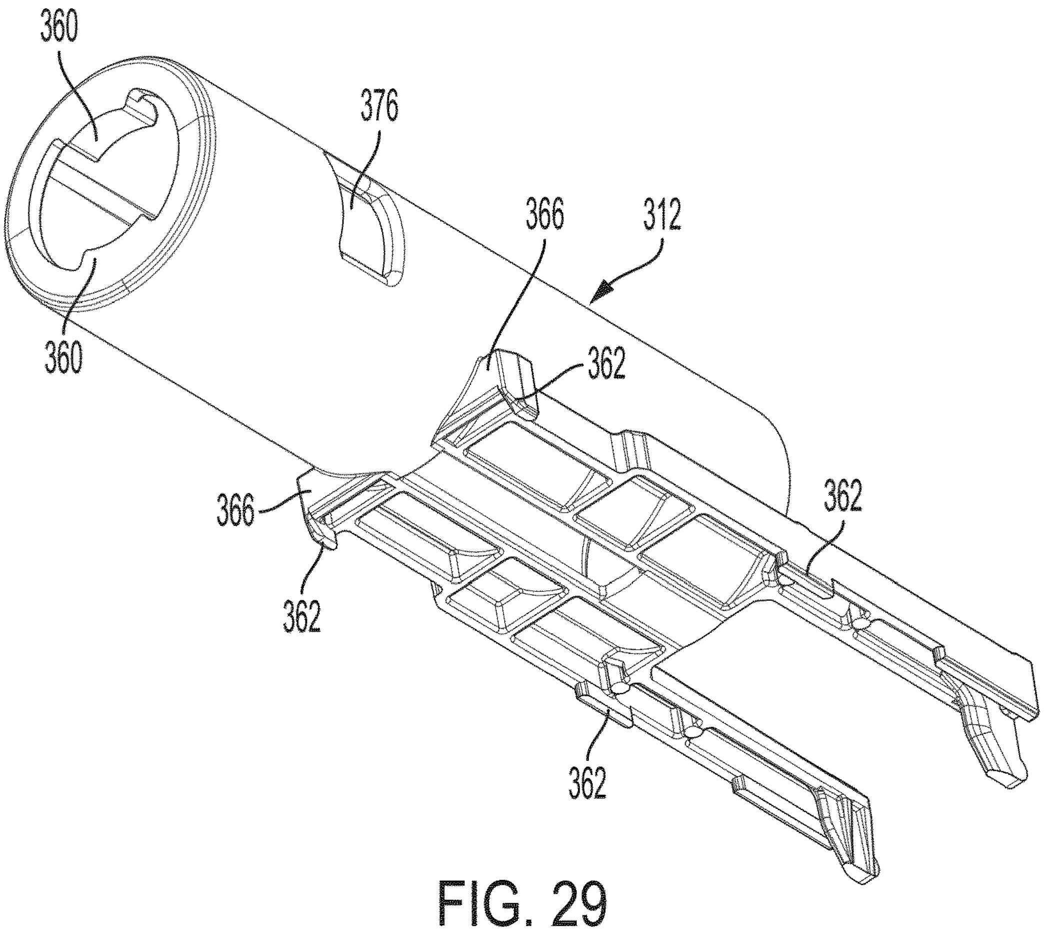
FIG. 29 is a front perspective view of a needle cover of the drug delivery device of FIG. 17.
Figure 30:
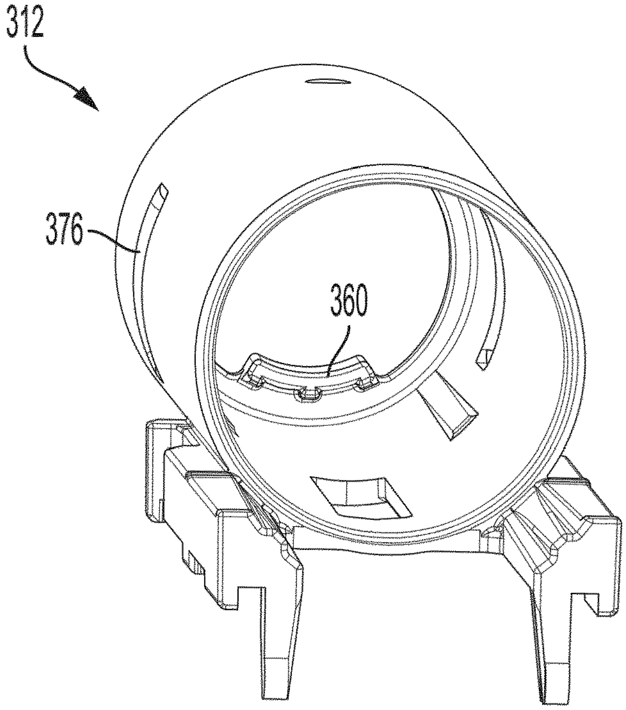
FIG. 30 is a rear perspective view of the needle cover of the drug delivery device of FIG. 29.
Figure 31:
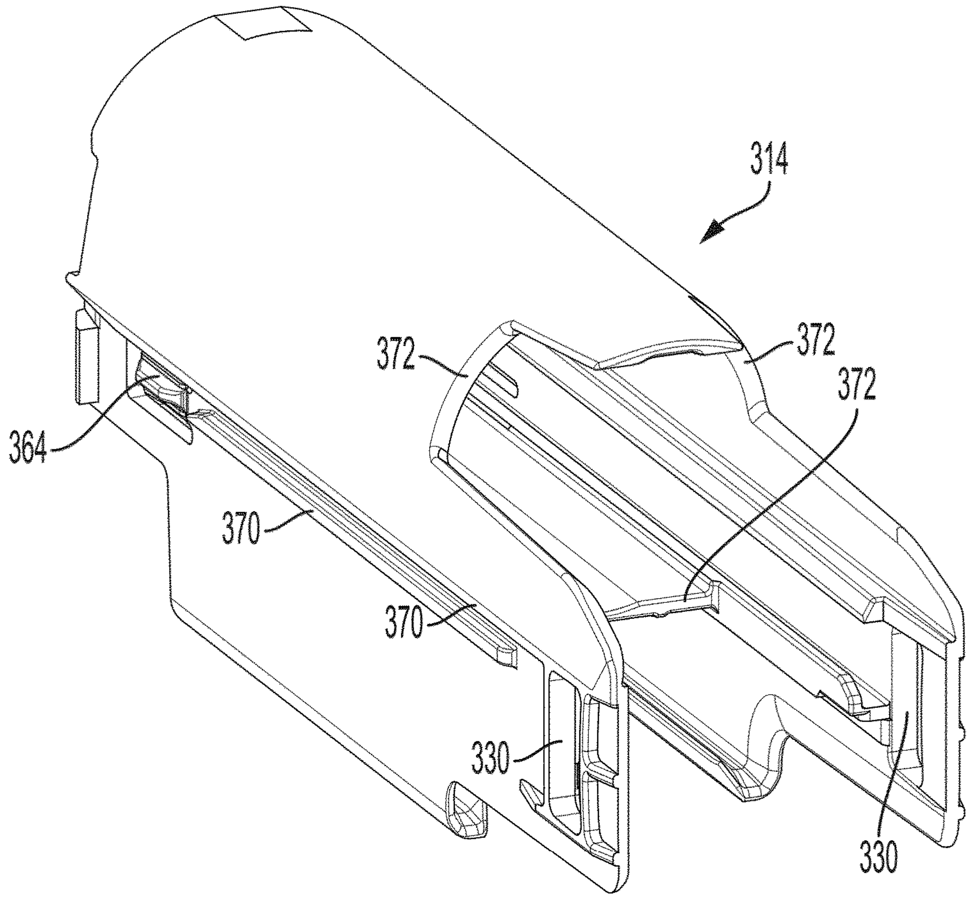
FIG. 31 is a top perspective view of a cassette body of the drug delivery device of FIG. 17.
Figure 32:
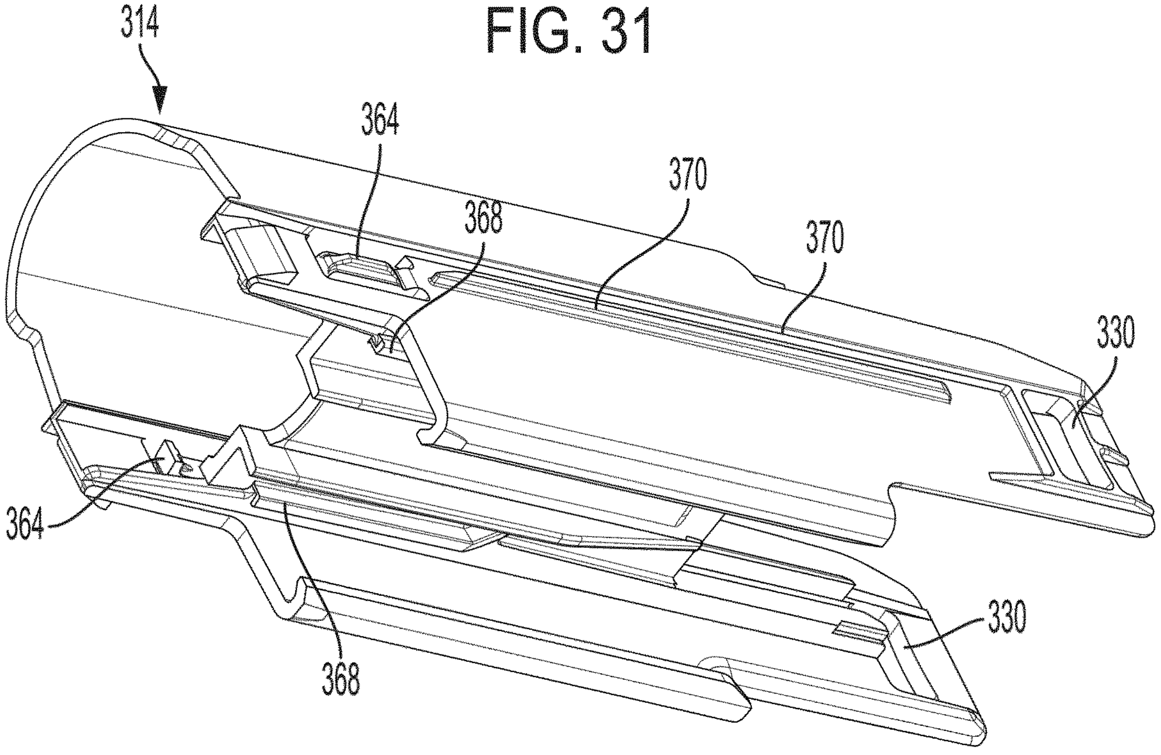
FIG. 32 is a bottom perspective of the cassette body of the drug delivery device of FIG. 31.
Figure 33:
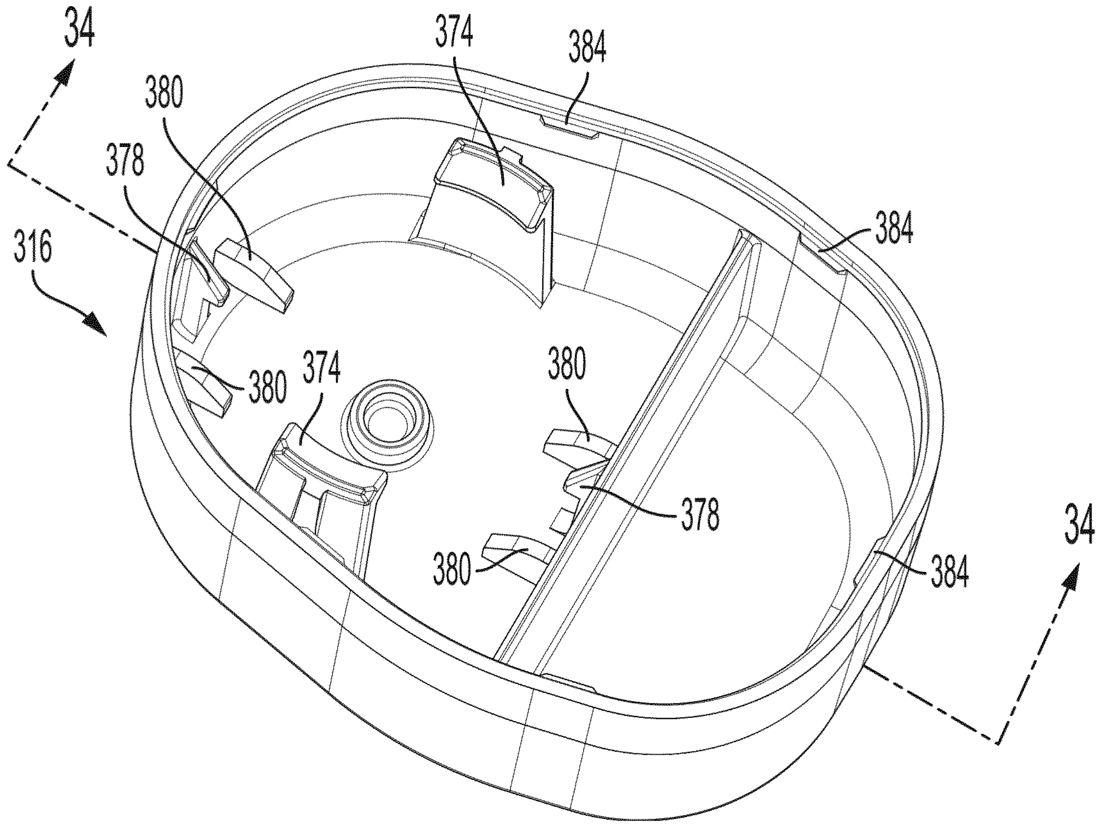
FIG. 33 is a top perspective view of a cap of the drug delivery device of FIG. 17.
Figure 34:
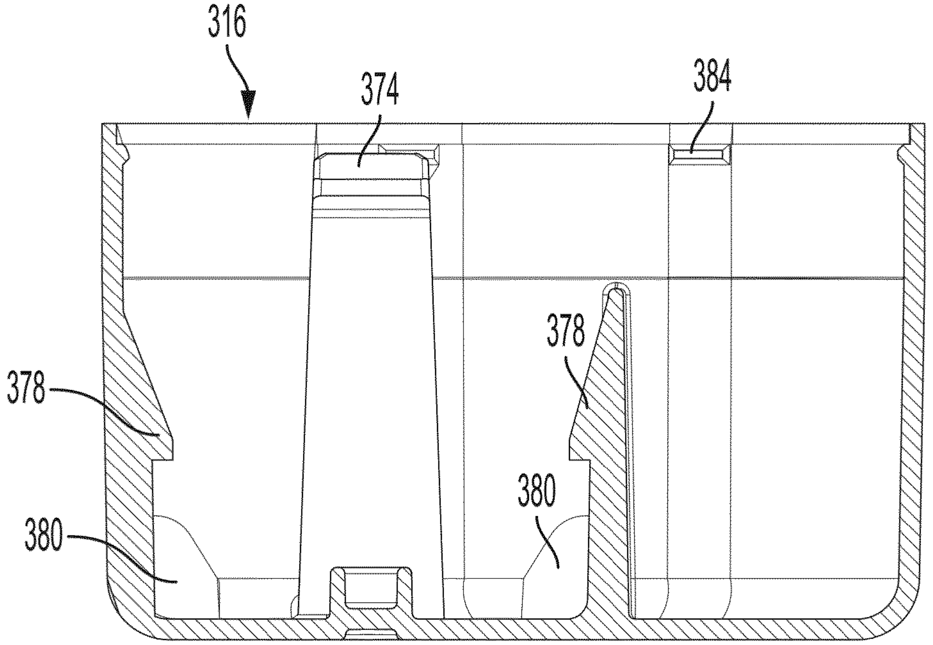
FIG. 34 is a cross-sectional view taken along line 34-34 in FIG. 33.
Figure 35:
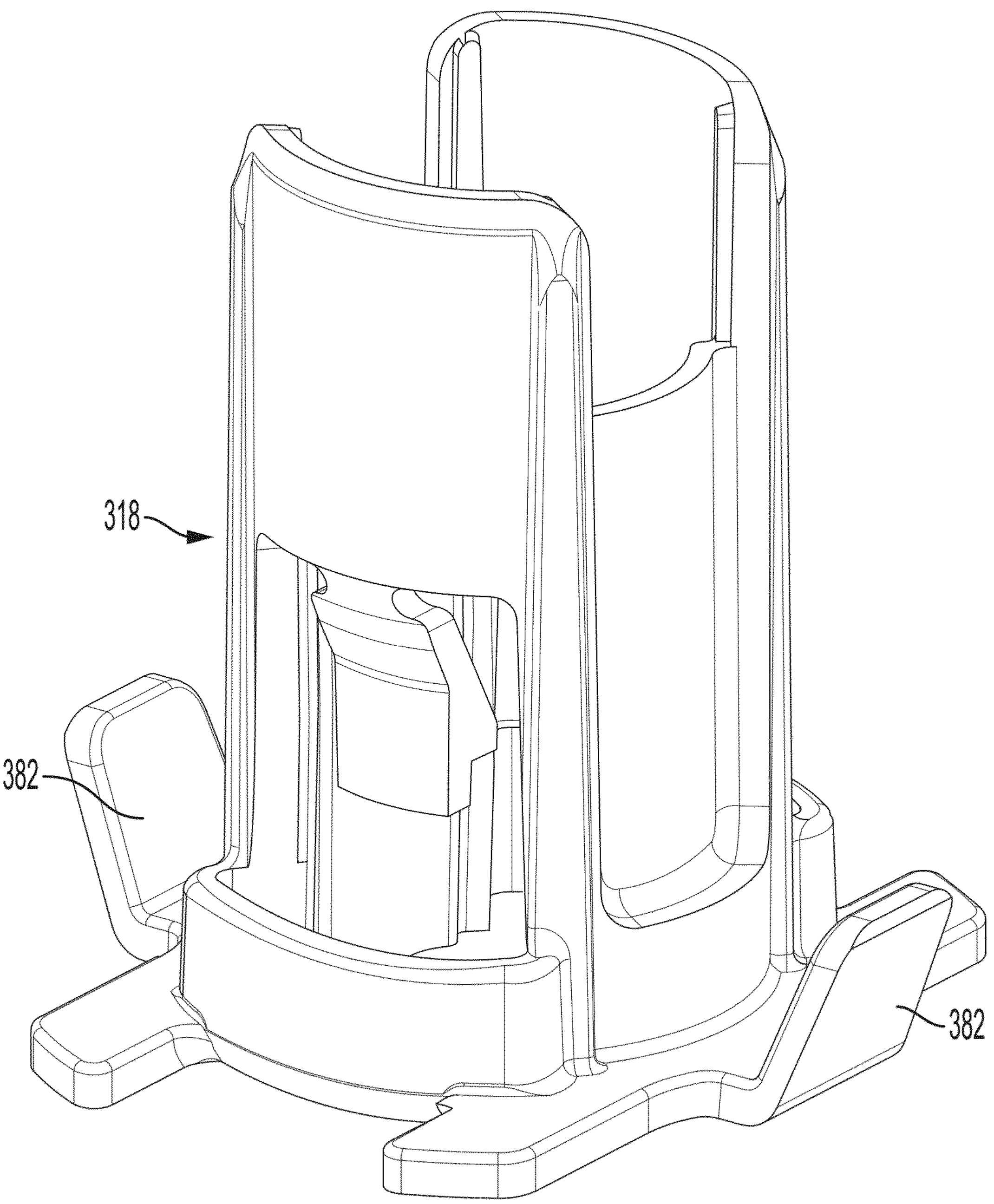
FIG. 35 is a perspective view of a retainer of the drug delivery device of FIG. 17.
Figure 36:
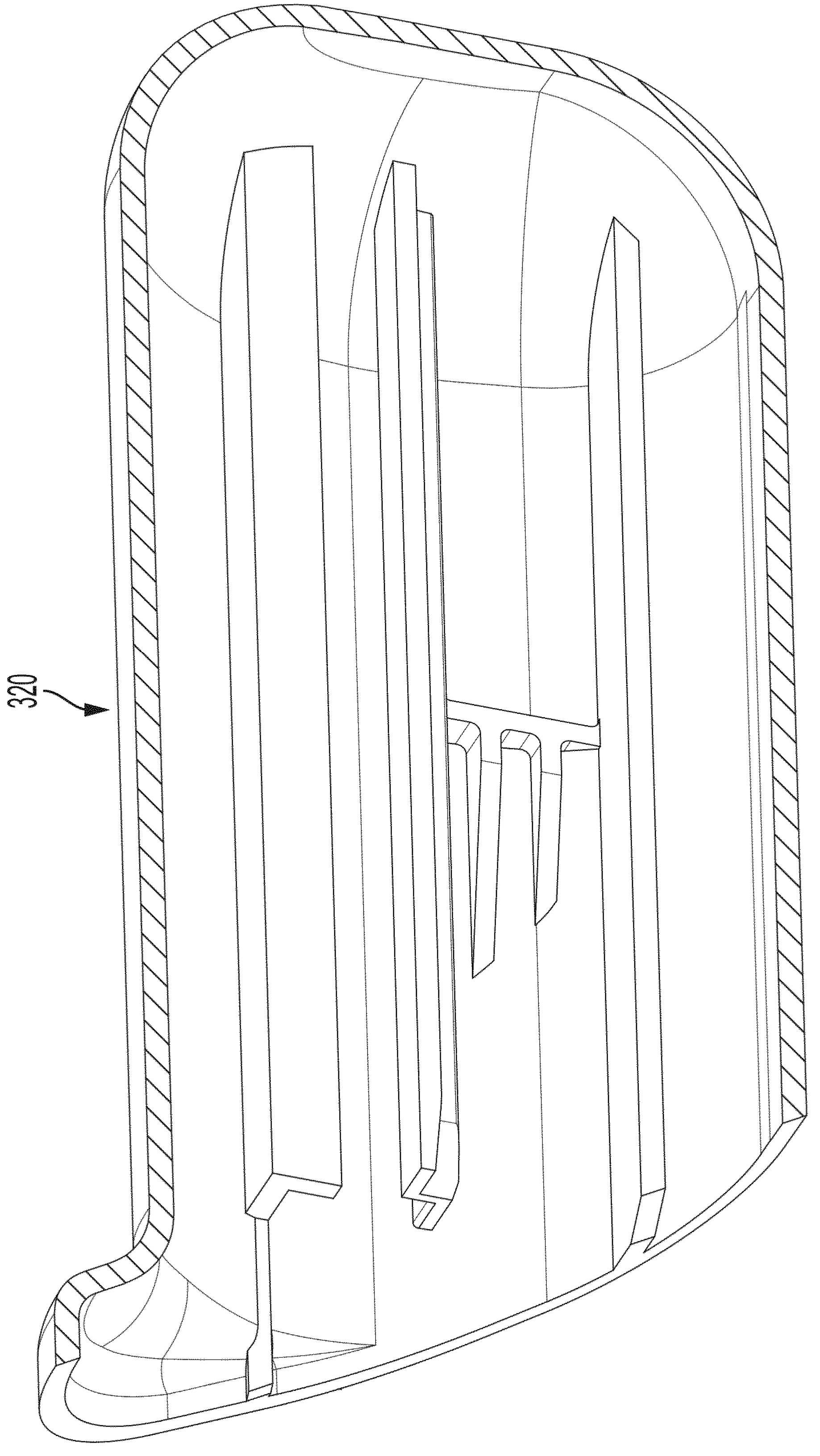
FIG. 36 is a cross-sectional view of an upper housing shell of the drug delivery device of FIG. 17.
Figure 37:
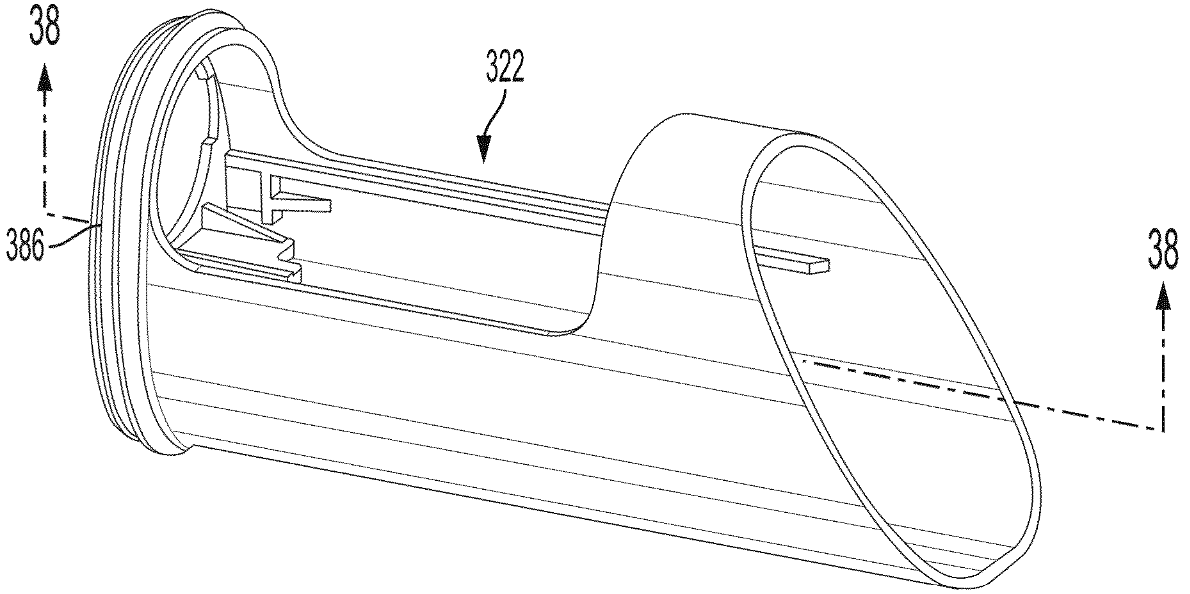
FIG. 37 is perspective view of a lower housing shell of the drug delivery device of FIG. 17.
Figure 38:
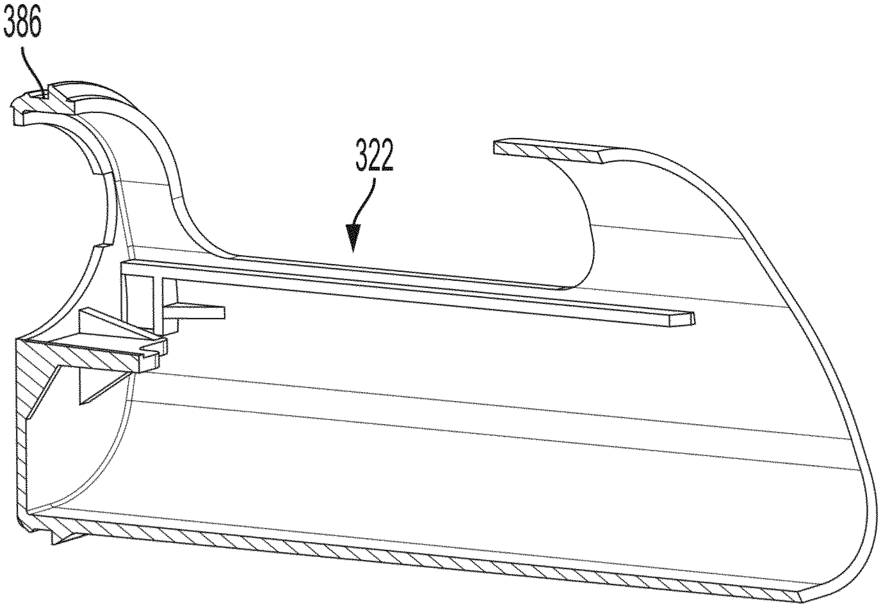
FIG. 38 is a cross-sectional view taken along line 38-38 in FIG. 37.

Referring to FIGS. 29 and 30, the needle cover 312 is similar to and functions similarly to the needle cover 22 of FIGS. 1A-16. The needle cover 312 includes a spring rib 360 which engages the spring 68 to hold the spring 68 between the needle cover 312 and the syringe holder 310. The needle cover 312 also includes a cassette rib(s) 362 to guide movement of the needle cover 312 relative to the cassette body 314.

Referring to FIGS. 31, 32, 40, and 41, the cassette body 314 is similar to and functions similarly to the cassette body 26 of FIGS. 1A-16. As discussed above, the cassette body 314 includes the opening(s) 330 that receive the cassette clip(s) 328 of the motor body 302. The cassette body 314 includes a needle cover clip(s) 364 that engage clip surface(s) 366 of the needle cover 312. The clip surface(s) 366 of the needle cover 312 are planar, although other suitable shapes and configurations may be utilized. The needle cover clip(s) 364 are configured to restrict the axial movement of the needle cover 312 relative to the cassette body 314. The cassette body 314 further includes motor body rib(s) 368 and upper housing shell rib(s) 370, which are configured to engage corresponding portions of the motor body 302 and the upper housing shell 320 to aid in the assembly of the device 300. The cassette body 314 also includes syringe holder stop(s) 372, which are configured to engage portions of the syringe holder 310 to limit the axial movement of the syringe holder 310 relative to the cassette body 314. Although not shown in FIG. 40, the locking clip 64 may also be utilized with the drug delivery device 300.

Referring to FIGS. 33-38, the cap 316 is similar to and functions similarly to the cap 18 described above and shown in FIGS. 1A-16. The cap 316 includes a protrusion(s) 374 that is received by a cap opening(s) 376 defined by the needle cover 312, which is positioned 90 degrees relative to the position of those elements of the cap 18 of FIGS. 1A-16. The protrusion(s) 374 of the cap 316 is configured to engage the needle cover 312 upon movement of the needle cover 312 from the pre-use position to the actuation position. For instance, with the device 300 in the storage position with the cap 316 secured to the lower housing shell 322, if the device is dropped or impacted to apply a force to the needle cover 312, the lever actuation member 308, and/or other component, the protrusion(s) 374 restricts movement of the needle cover 312, which prevents any unintended actuation of the device 300. The cap 316 further includes a retainer clip(s) 378 and a rib(s) 380 for engaging a wing(s) 382 of the retainer 318. The retainer clip(s) 378 and the rib(s) 380 secure the retainer 318 to the cap 316 and prevent any movement or wobbling of the retainer 318 relative to the cap 316. The retainer 318 is configured to remove the RNS 58 when the cap 316 is removed from the lower housing shell 322. The cap 316 includes a lower housing shell clip(s) 384 for engaging the lower housing shell 322 to secure the cap 316 to the lower housing shell 322. The upper housing shell 320 and the lower housing shell 322 are similar and function similarly to the upper housing shell 46 and the lower housing shell 28 discussed above and shown in FIGS. 1A-16. The lower housing shell 322, however, has a cap interface 386 to receive the lower housing shell clip(s) 384 of the cap 316.

Figure 39:
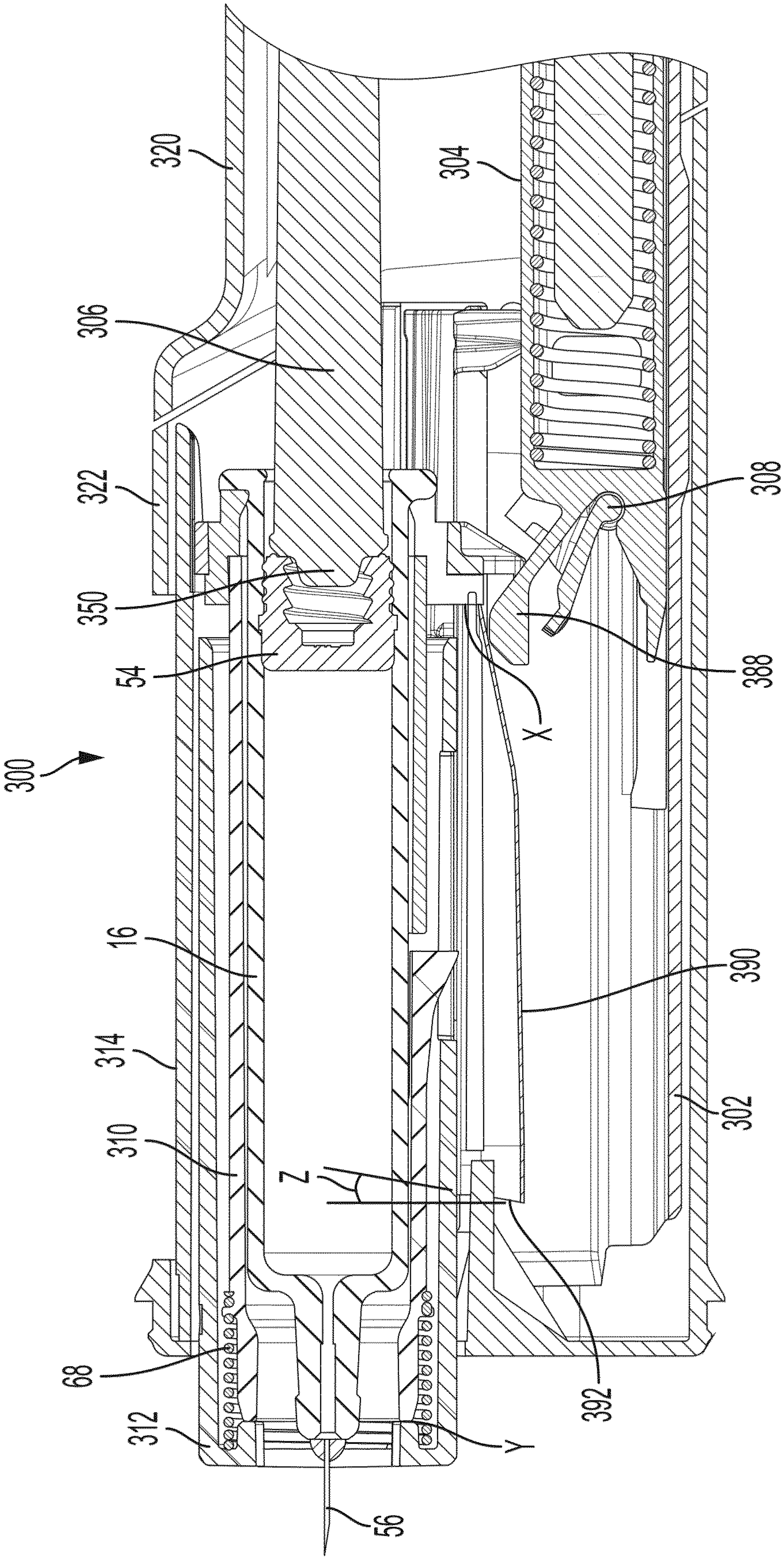
FIG. 39 is a cross-sectional view of the drug delivery device of FIG. 17, showing an injection position of the device.
Figure 40:
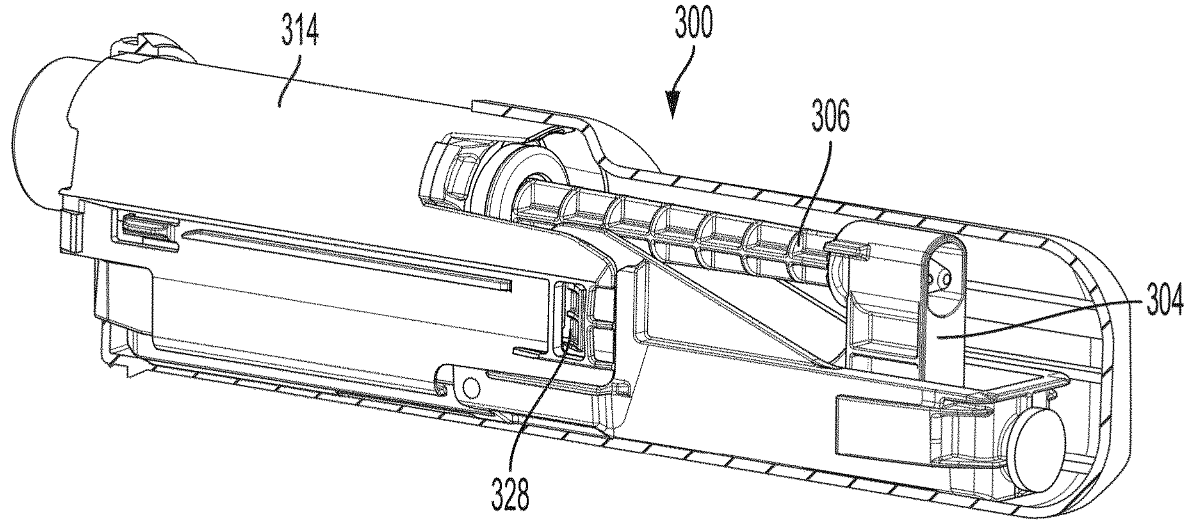
FIG. 40 is a partial cross-sectional view of the drug delivery system of FIG. 17.
Figure 41:
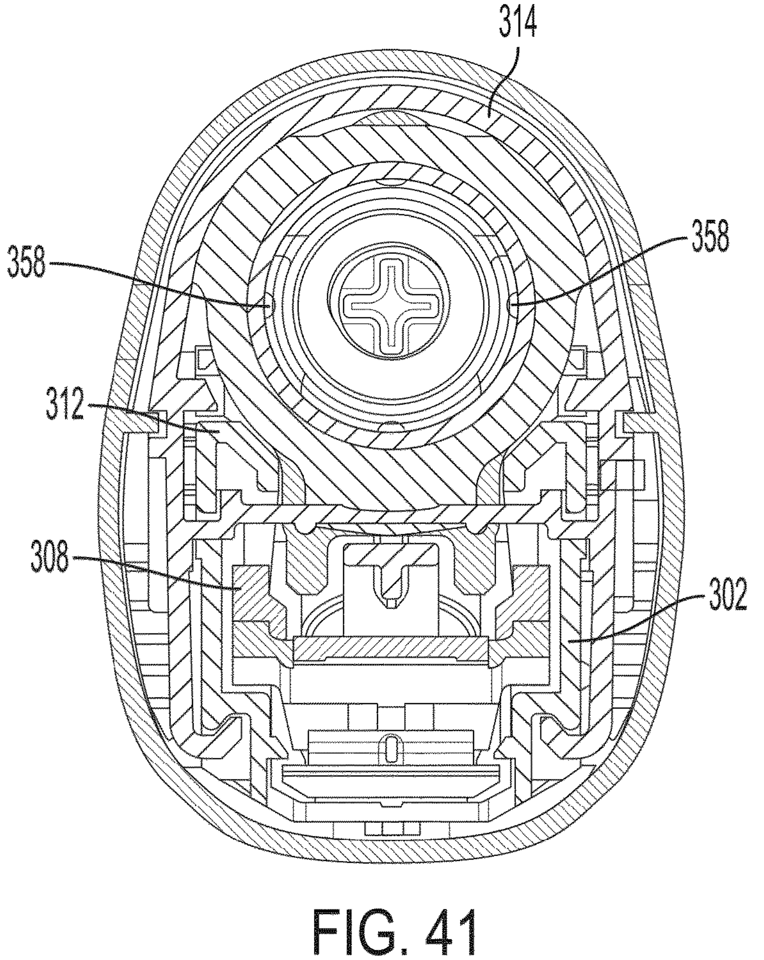
FIG. 41 is a cross-sectional view of the drug delivery system of FIG. 17.

Referring to FIG. 39, the drug delivery device 300 is shown in an injection position. The injection depth of the cannula 56 is determined by contact between the syringe holder 310 and the cassette body 314 at point X and contact between the needle cover 312 and the syringe holder 310 at point Y.

Referring to FIG. 39, the drug delivery device 300 includes an audio indicator member 388, which is similar to and functions similarly to the audio indicator member 94 described above and shown in FIGS. 1A-16. In the same manner as the audio indicator member 94, which is described above, the audio indicator member 388 of the drug delivery device 300 is configured to provide an audible indication to a user when the device 300 transition to the post-use position. The audio indicator member 388 is configured to engage rib(s) 390 of the cassette body 314 when the device 300 is in the injection position thereby deflecting the audio indicator member 388. The audio indicator member 388 disengages from the rib(s) 390 of the cassette body 314 and contacts the lower housing shell 322 to provide an audible click when the drug delivery device 300 transition from the injection position to the post-use position. However, a distal end 392 of the rib(s) 390 of the cassette body 314 is angled rearward toward the upper housing shell 320, which beneficially provides a louder audible click compared to the arranged of the rib(s) 96 of the cassette body 26 discussed above in connection with FIGS. 1A-16.

In one aspect or embodiment, an angle Z of the distal end 392 of the rib(s) 390 of the cassette body 314 relative to a plane extending perpendicularly to a longitudinal axis of the device 300 is greater than 5 degrees. In one aspect or embodiment, the angle Z of the distal end 392 of the rib(s) 390 is greater than 10 degrees. In one aspect or embodiment, the angle Z of the distal end 392 is 25 degrees.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery device comprising:

a housing;

a syringe assembly comprising a barrel, a stopper, and a cannula, at least a portion of the syringe assembly positioned within the housing;

a drive assembly comprising a plunger body configured to move the stopper within the barrel upon actuation of the drive assembly, at least a portion of the drive assembly positioned within the housing, the plunger body having a pre-use position prior to movement of the plunger body, an injection position where the plunger body moves the stopper within the barrel, and a post-use position where movement of the plunger body has stopped;

an audio indicator member connected to the plunger body, and a syringe holder moveable relative to the housing, wherein the audio indicator member is configured to restrict movement of the syringe holder when the plunger body is in the pre-use position;

wherein the housing comprises a rib extending in a longitudinal direction of the device, the audio indicator member engaging the rib when the plunger body is in the injection position to deflect the audio indicator member from an unbiased position to a biased position, the audio indicator member disengaging from the rib and contacting a portion of the housing when the plunger body reaches the post-use position to cause an audible indication of a transition of the plunger body from the injection position to the post-use position.

2. The drug delivery device of claim 1, wherein the audio indicator member has a released position, the audio indicator member positioned in the biased position when the plunger body is in the injection position, the audio indicator member positioned in the released position when the plunger body is in the post-use position.

3. The drug delivery device of claim 2, wherein the audio indicator member is positioned in the unbiased position when the plunger body is in the pre-use position.

4. The drug delivery device of claim 1, wherein the housing comprises a lower housing shell, an upper housing shell, and a cassette body received by the lower housing shell, the lower housing shell comprises an indicator platform, the audio indicator member engaging the indicator platform to provide the audible indication.

5. The drug delivery device of claim 1, wherein the housing comprises a lower housing shell, an upper housing shell, and a cassette body received by the lower housing shell, the cassette body including the rib.

6. The drug delivery device of claim 5, wherein the rib extends only a portion of a length of the cassette body.

7. The drug delivery device of claim 1, wherein the rib comprises a sloped surface configured to transition the audio indicator member from the unbiased position to the biased position.

8. The drug delivery device of claim 1, wherein the audio indicator member is formed integrally with the plunger body.

9. The drug delivery device of claim 1, further comprising a visual indicator member configured to provide a visual indication of a transition of the plunger body from the injection position to the post-use position.

10. The drug delivery device of claim 9, wherein the visual indicator member is visible via an indicator opening defined by the housing when the plunger body is in the post-use position.

11. The drug delivery device of claim 10, wherein the housing comprises a lower housing shell, the lower housing shell defining the indicator opening.

12. The drug delivery device of claim 10, wherein the visual indicator member is formed integrally with the plunger body, the visual indicator member spaced from the audio indicator member.

* * * * *